United States Patent [19]

Mantri et al.

[11] Patent Number: 5,656,662
[45] Date of Patent: Aug. 12, 1997

[54] SYNTHESIS OF OPTICALLY PURE 4-ALKENYL- OR 4-ALKANYL-2-HYDROXYTETRONIC ACIDS

[75] Inventors: Padmaja Mantri, Newark, Del.; Donald T. Witiak, Madison, Wis.

[73] Assignee: The Ohio State University Research Foundation, Columbus, Ohio

[21] Appl. No.: 485,209

[22] Filed: Jun. 7, 1995

Related U.S. Application Data

[63] Continuation-in-part of Ser. No. 245,615, May 19, 1994, Pat. No. 5,504,107, which is a continuation-in-part of Ser. No. 201,775, Feb. 25, 1994, Pat. No. 5,399,721, which is a continuation-in-part of Ser. No. 847,295, Mar. 6, 1992, Pat. No. 5,298,526, which is a division of Ser. No. 464,511, Jan. 12, 1990, Pat. No. 5,095,126.

[51] Int. Cl.$^6$ ............. A61K 31/365; C07D 307/62
[52] U.S. Cl. ............. 514/473; 514/474; 549/315; 549/316
[58] Field of Search ............. 549/315, 316; 514/473, 474

[56] References Cited

U.S. PATENT DOCUMENTS

| | | | |
|---|---|---|---|
| 5,008,405 | 4/1991 | Hatanaka et al. | 549/315 |
| 5,095,126 | 3/1992 | Witiak et al. | 549/315 |
| 5,298,526 | 3/1994 | Witiak et al. | 514/473 |
| 5,399,721 | 3/1995 | Hopper | 549/315 |
| 5,504,107 | 4/1996 | Mantri et al. | 514/473 |

OTHER PUBLICATIONS

Haynes et al., "Tetronic Acids" *Chem. Soc.: Quart. Rev.*, 1960, 292–315.

Ireland and Thompson, "An approach to the total synthesis of chlorothrieolide: the synthesis of the top half" *J. Org. Chem.*, 1979, 44:3041–3052.

Kamanna et al., "Serum lipoprotein and apoprotein concentrations in 4-(4-chlorophenyl)-2-hydroxytetronic acid and clofibrate-treated cholesterol and cholic acid-fed rats" *Lipids*, 1989, 24:25–32.

Schank, "Reductones," *Synthesis*, 1972, 176–190.

Triozzi et al., "Aci-reductones enhance interleukin-2-induced lymphocytic cytotoxicity" *Int. J. Immunopharmac.*, 1993, 15:47–54.

Witiak et al., "4-substituted-2-hydroxytetronic acid aci-reducones improve lymphokin-activated killer cell activity in vitro" *Proc. Am. Assoc. Canc. Res.*, 1993, Florida, (#2665).

Witiak et al., "Chemical Approaches to the treatment of artherosclerosis" in Trends in Medicinal Chemistry, Blackwell Scientific Publications: Oxford, 1990, pp. 243–256.

Witiak et al., "Efficient synthesis for optically pure stereogenically labile 4-substituted-2-hydroxytetronic acids" *J. Org. Chem.*, 1990, 55:1112–1114.

Witiak et al., "Medicinal chemistry aspects of antilipidemic drugs: acireductone antilipidemic and antiaggregatory agents" *Actual Chem. Ther.*, 1988, 15:41–62.

Witiak et al., "Synthetic aci-reductones: 3,4-dihydroxy-2H-1-benzopyran-2-ones and their trans-4a,5,6,7,8,8a-hesahydro diastereomers" *J. Med. Chem.*, 1988, 31:1437–1445.

Witiak and Tehim, "Synthetic approaches to 4-spiro-2-hydroxytetronic acids" *J. Org. Chem.*, 1987, 52:2324–2327.

Witiak et al., "Hypocholesterolemic and antiaggregatory properties of 2-hydroxytetronic acid redox analogues and their relationship to clofibric acid" *J. Med. Chem.*, 1986, 29:2170–2174.

Witiak et al., "Comparative antiaggregatory activity in human platelets of a benzopyranone aci-reductone, clofibric acid, and a 2,3 dihydrobenzofuran analogue" *J. Med. Chem.*, 1982, 25:90–93.

*Primary Examiner*—Richard L. Raymond
*Attorney, Agent, or Firm*—Klauber & Jackson

[57] ABSTRACT

The present invention relates to a method for synthesis of optically pure 4-alkenyl or 4-alkanyl-2-hydroxytetronic acids from an optically pure aldehyde. The invention further relates to the use of such optically pure compounds as potent inhibitors of platelet aggregation by working at the level of cyclooxygenase, thus making them useful in the treatment of coronary artery diseases, especially atherosclerosis, and additionally, as inhibitors of various inflammatory cytokines, making them useful in the treatment of both acute and chronic inflammation, as well in the treatment of cachexia, rheumatoid arthritis, multiple sclerosis, Crohn's disease and ulcerative colitis. The invention further relates to pharmaceutical compositions of the instant compounds.

34 Claims, No Drawings

SYNTHESIS OF OPTICALLY PURE 4-ALKENYL- OR 4-ALKANYL-2-HYDROXYTETRONIC ACIDS

This application is a Continuation-In-Part of U.S. Ser. No. 08/245,615, filed May 19, 1994, now U.S. Pat. No. 5,504,107, which is a Continuation-In-Part of U.S. Ser. No. 08/201,775, filed Feb. 25, 1994, now U.S. Pat. No. 5,399,721; which is a Continuation-In-Part of U.S. Ser. No. 07/847,295, filed Mar. 6, 1992, now U.S. Pat. No. 5,298,526; which is a division of U.S. Ser. No. 07/464,511, filed Jan. 12, 1990, and now U.S. Pat. No. 5,095,126.

BACKGROUND OF THE INVENTION

The present invention relates generally to methods for the synthesis of optically pure 4-alkenyl- or 4-alkanyl-2-hydroxytetronic acid aci-reductone compounds.

The aci-reductone, 4-(4-chlorophenyl)-2-hydroxytetronic acid compound (CHTA), possesses antilipidemic and antiaggregatory properties which differ from those of the classical phenoxyacetic acids as has been disclosed in Witiak et al. *J. Med. Chem.*, 1988, 31:1437–1445 and Kamanna et al., *Lipids*, 1989, 24:25–32. Although unsubstituted-, 2-alkanyl- and 2-acyltetronic acids are frequently found in nature, the 2-hydroxy substituted redox system is found only in vitamin C and its closely related relatives (isoascorbic acid, erythroascorbic acid) and derivatives, and the macrolide antibiotic chlorothricin.

The antiaggregatory activities of 2-hydroxytetronic acid aci-reductone compounds such as CHTA are of interest since blood platelets are involved in the genesis of atherosclerosis. 2-Hydroxytetronic acid aci-reductones inhibit cyclooxygenase (CO)-induced human platelet aggregation and secretion of [$^{14}$C]-serotonin in a concentration-dependent manner at equivalent doses, as reported in Witiak et al., *J. Med. Chem.*, 1982, 25:90–93.

The CHTA compound inhibits platelet function by both enzyme inhibitory and ROS scavenging mechanisms resulting ultimately in the blockage of thromboxane $A_2$ synthesis. Redox analogues, such as 2-hydroxytetronic acid, may function as antioxidants in membranes and interfere with free radical processes involved in the biosynthetic elaboration of cyclic prostaglandin endoperoxides ($PGG_2$ and $PGH_2$), and, subsequently, thromboxane $A_2$ from arachidonic acid.

aci-Reductones, such as CHTA, possess numerous biological properties and have potentially many therapeutic applications. They exhibit antilipidemic and antithrombotic activities and increase the effectiveness of IL-2 promoted lymphokine-activated killer (LAK) cell activity in human peripheral blood mononuclear cells (PBMC).

aci-Reductones inhibit CO-dependent AA-induced platelet aggregation. See Witiak et al., *J. Med. Chem.*, 1982, 25:90–93; Witiak et al., 1988, *J. Med. Chem.*, 31:1437–1445 and Witiak et al., *J. Med. Chem.*, 1986, 29:2170–2174. A positive linear free energy relationship is observed between enzyme inhibition and calculated hydrophobicity ($\pi$) parameters. Thus, 4-biphenyl and 4-(4'-chlorobiphenyl)-2-hydroxytetronic acids possess an estimated '$\pi$' of 1.96 and 2.67 and inhibit AA-induced platelet aggregation with $IC_{50}$s of 135 and 44 µM, respectively.

4-Aryl-2-hydroxytetronic acids potentiate IL-2-induced LAK activity. This activity is related in part to CO inhibition. Highly tumoricidal lymphocytes induced by IL-2 have therapeutic potential in the treatment of cancers for which conventional antineoplastic therapy is not useful. The by-products of IL-2 activation, $PGE_2$ and reactive oxygen species (ROS) such as superoxide anion radical, abrogate LAK activity. aci-Reductones such as 4-aryl-, 4-alkanyl- and 4,4-spiroalkanyl-2-hydroxytetronic acids inhibit CO and the production of $PGE_2$ as well as scavenge ROS, thus improving IL-2-induced LAK activity. In standard 4-hour $^{51}Cr$ release assays, the improvement in LAK activity observed is comparable to the combined synergy obtained using the CO inhibitor indomethacin and ROS scavenging enzymes superoxide dismutase (SOD) and catalase. See, Triozzi et al., *Int. J. Immunopharmac.*, 1993, 15:47–54 and Witiak et al., *Am. Canc. Res. Mtg.*, 1993, Florida. Thus, aci-reductones may be useful in potentiating IL-2 cancer therapy.

aci-Reductones are also antilipidemic and lower total serum cholesterol, triglycerides, VLDL, and LDL in cholesterol/cholic acid-fed rats. These compounds have been found to decrease apoB in VLDL in vivo and inhibit copper-catalyzed LDL oxidation in vitro. See, Witiak et al., *J. Med. Chem.*, 1982, 25:90–93, (1982); Witiak et al., *Actual Chem. Ther.*, 1988, 15:41–62 (1988) and Witiak et al., *J. Med. Chem.*, 1988, 31:1437–1445.

Free-radicals play a significant role in UV-, drug- and xenobiotic-induced toxicities and activate molecular oxygen to superoxide and other ROS including hydrogen peroxide and hydroxyl radical. Defense mechanisms, including enzymes such as SOD and catalase and radical scavengers such as glutathione, retinoic acid and ascorbic acid protect proteins and nucleic acids from free-radical toxicities by quenching ROS. Inadequate protection from ROS results in myocardial ischemia, photosensitivity, radiation sensitization, red cell hemolysis and atherosclerosis. 4-Aryl-2-hydroxytetronic acids have been found to possess antioxidant efficiencies similar to probucol and $\alpha$-tocopherol. See Witiak et al., "Trends in Medicinal Chemistry", pp. 243–256, Blackwell Scientific Publications: Oxford, 1990.

Syntheses for 2-hydroxytetronic acids other than ascorbic acid have been reviewed by Haynes and Plimmer in "Tetronic Acids," *Quart. Rev.*, 1960, 292–315, and by Shank, "Reductones," *Synthesis*, 1972, 176–190. 2-Hydroxytetronic acids have generally been prepared using three different routes: (1) hydroxyl group insertion at the 2 position of the corresponding tetronic acid nucleus; (2) intramolecular Claisen cyclization of substituted glyoxylate esters; and (3) base-promoted cyclization of 2,4-dihydroxy-3-ketobutanoates.

Witiak and Tehim, *J. Org. Chem.*, 1987, 52:2324–2327 synthesized the 5- and 6-membered spiro 2-hydroxytetronic acids using propargyl alcohol conversion to methyl spirotetronates by treatment with sodium methoxide. Attempted hydroxylation at the 2-position by $\alpha$-lithiation and reaction with dibenzoylperoxide provided only a 6% yield of the corresponding 2-benzoyloxytetronic acid. However, the 2-hydroxyl group was introduced in good yields by lithiation using lithium diisopropylamide (LDA), boronate ester formation [$B(MeO)_3$] and oxidative hydrolysis ($AcOH$, $H_2O_2$). Methyl 2-hydroxytetronate was converted to the corresponding aci-reductone by stirring in 48% HBr at 45° C. for 12 hours. Ireland and Thompson, *J. Org. Chem.*, 1979, 44:3041–3052, utilized the Claisen condensation for construction of 2-hydroxytetronic acids.

Witiak and Tehim, *J. Org. Chem.*, 1987, 52:2324–2327 prepared 5- and 6-membered spiro-2-hydroxytetronic acids using strategies developed by Ireland and Thompson, supra. This method was superior to use of hydroxyl group insertion methods because fewer steps were necessary and overall yields were higher. For example, intramolecular Claisen cyclization of easily prepared methoxy or benzyloxy thiocarboxylate intermediates using LDA or lithium hexamethyldisilazide (LiHMDA) at −78° C. occurred in high yields. The resultant 2-methoxytetronic acids underwent deprotection by acetylation and subsequent reaction with $BBr_3$, whereas the 2-benzyloxytetronic acids were convertible to target 2-hydroxytetronic acids by transfer hydrogenation.

Witiak and Tehim, *J. Org. Chem.*, 1990, 55:1112–1114 developed the first synthesis for optically pure (S)-(+)-4-phenyl-2-hydroxytetronic acid using the Claisen cyclization under kinetically controlled conditions. The 2-benzyloxymethoxyacetate derivative of the corresponding methyl mandelate underwent such cyclization at −100° C. using the sterically hindered non-nucleophilic base, lithium dicyclohexylamide (LiDCyA). Subsequent benzyl group deprotection of the tetronic acid generated the desired compound in low overall yields; 12% for both steps.

U.S. Pat. No. 5,095,126 and U.S. application Ser. No. 07/847,295, now U.S. Pat. No. 5,298,528, relate to the preparation of optically pure stereogenically labile 4-substituted-2-hydroxytetronic acid compounds.

SUMMARY OF THE INVENTION

The present invention relates to optically pure 4-alkenyl- or 4-alkanyl-2-hydroxytetronic acids and processes for their preparation. The chiral approach of the present invention utilizes a Claisen condensation of optically pure methyl 2-alkanyl or 2-alkenyl-substituted 2-[(2-allyloxy)acetyloxy]acetate to generate 4-alkanyl or 4-alkenyl substituted 2-allyloxytetronic acids. Deprotection provides target aci-reductones.

The invention is further related to the methods of using such optically pure compounds as potent inhibitors of platelet aggregation, and pharmaceutical compositions therefor.

The invention is further concerned with the pharmaceutical use of such compositions for the treatment and/or the prevention of coronary artery diseases, platelet aggregation and thrombosis, and/or prevention of atherosclerosis.

DETAILED DESCRIPTION OF THE INVENTION

In a first embodiment, the present invention relates to optically pure 4-alkenyl- or 4-alkanyl-2-hydroxytetronic acid compounds of the general formulae Ia or Ib

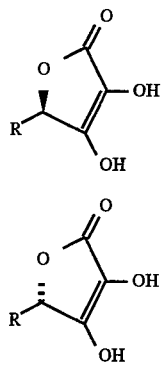

wherein R is an alkenyl group of 2–20 carbon atoms or an alkanyl group of 9–20 carbon atoms, and, when an alkenyl group, contains one or more degrees of unsaturation.

In a composition aspect, the present invention encompasses novel pharmaceutical compositions comprising the optically pure compound of the general formulae Ia and Ib, together with a physiologically acceptable carrier or excipient, in an amount sufficient to have antilipidemic or antiaggregatory activities in an animal or patient. The compounds and their compositions of the present invention are thus useful in the treatment or prevention of atherosclerotic disorders.

As used herein, the term "alkenyl group of 2–20 carbon atoms containing one or more degrees of unsaturation" means an organic, alkanyl group containing one or more double bonds and which can optionally be substituted by one or more halogen, lower alkanyl, alkoxy, aromatic or heteroaromatic groups. Examples of unsubstituted alkenyl groups include those such as 3-octadecenyl, 3,6,9,12-octadecatetraenyl, and the like. Examples of alkanyl groups of 9–20 carbon atoms include hexadecanyl, heptadecanyl, octadecanyl, nonadecanyl and eicosanyl, as well as their corresponding branched-chain analogs thereof.

Examples of substituted lower alkenyl groups include those such as halogen substituted alkenyl, e.g., fluoro, chloro, bromo and iodo-substituted alkenyl; alkanyl-substituted alkenyl, e.g., methanyl-, ethanyl and similar alkenyl; and alkoxy substituted alkenyl, e.g., methoxy, ethoxy and similar-alkenyl.

As used herein, the term "lower alkanyl" means straight- or branched-chain saturated aliphatic hydrocarbon groups preferably containing 1–6 carbon atoms. Representative of such groups are methyl, ethanyl, isopropanyl, isobutanyl, butanyl, pentanyl, hexanyl and the like.

The term "alkoxy" means a lower alkanyl group attached to the remainder of the molecule by oxygen. Examples of alkoxy are methoxy, ethoxy, propoxy, isopropoxy and the like. The term "aryl" means phenyl or benzyl, optionally substituted by one or more halogen atoms, e.g., fluoro, chloro, bromo or iodo, or lower alkanyl groups.

A second embodiment of the present invention relates to a process for making optically pure 4-substituted-2-hydroxytetronic acid compounds of formula I:

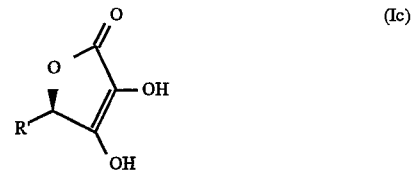

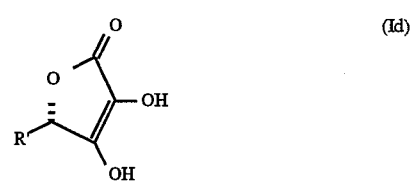

wherein R' is an alkenyl or alkanyl group of 2–20 carbon atoms, and, when an alkenyl group, contains one, or more degrees of unsaturation, or an aryl group.

This process comprises:

(a) coupling of α-allyloxyacetic acid with the optically pure alkanyl ester of the formula II

or its corresponding isomer, wherein R' is as hereinbefore defined and alk is a lower alkanyl group of 1–6 carbon atoms in the presence of DCC (N,N¹-dicyclohexylcarbodiimide) and an acid acceptor such as 4-pyrrolidinopyridine or dimethyl aminopyridine, to obtain an α-allyloxy acetyl ester of the formula III

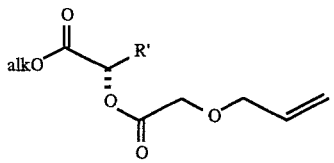

(III)

or its corresponding isomer, wherein alk and R' are as hereinbefore defined;

(b) cyclizing the allyl ester of formula III with LiHMDA to afford the allyloxy aci-reductone of the formula IV

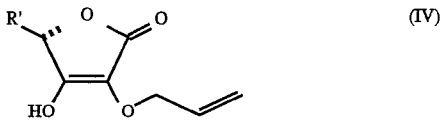

(IV)

wherein R' is as hereinbefore defined, or its corresponding isomer;

(c) isomerizing the allyloxy aci-reductone of formula IV with hydrogen and an iridium catalyst to yield the corresponding 1-propenyl ether of the formula V

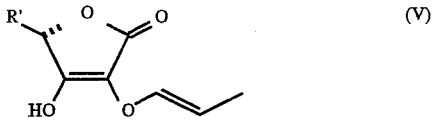

(V)

or its corresponding isomer, wherein R' is as hereinbefore defined; and (d) hydrolysis of the enol ether of formula V, or its corresponding isomer with aqueous acid, to afford the desired compound of formula I.

The coupling of step (a) is typically conducted in an anhydrous solvent, such as methylene chloride, under an inert atmosphere. Preferably, the reaction is conducted at temperatures of about 5° C. to room temperature, for periods of 6–24 hours. The coupling reagents used are preferably DCC or hydroxybenzotriazine (HOBT) or the like in combination with a catalytic nucleophile such as 4-(N,N-dimethylamino)pyridine (DMAP), 4-pyrrolidinopyridine or another typically utilized for this purpose.

The cyclization of step (b) is typically conducted in an anhydrous solvent such as tetrahydrofuran under an inert atmosphere. Preferably, this reaction is conducted at temperatures of about −78° C. for periods of 1–4 hours. LiHMDA is typically utilized as a sterically hindered non-nucleophilic base, but other similar sterically hindered bases can be substituted.

The isomerization of step (c) is preferably conducted in an anhydrous solvent, such as tetrahydrofuran, under an inert atmosphere. Typically, the reaction is conducted at room temperatures, with reaction times being, approximately 1–4 hours.

The hydrolysis of step (d) is conducted with an aqueous acid, preferably 50% acetic acid, at reflux temperatures.

The invention also provides for pharmaceutical compositions comprising the optically pure compounds of the general formula I above, as well as their physiologically acceptable salts (such as, for example, $Na^+$, $K^+$, $NH_4^+$).

The compounds of the invention have antilipidemic and antiaggregatory activity and are useful in the treatment or prevention of atherosclerotic disorders. The invention accordingly further provides optically pure compounds of the general formula I and their physiologically acceptable salts for use in the therapy or prophylaxis of atherosclerotic disorders.

When tested according to the methods described in the art, the (S)-isomers of formula Ib having the formula

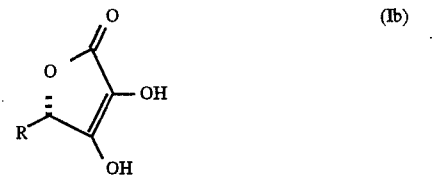

(Ib)

wherein R is as hereinbefore defined, have been found to possess markedly superior properties when compared to their corresponding (R)-isomers.

The R- and S-enantiomers were tested as inhibitors of arachidonic acid-induced aggregation in human platelet-rich plasma. Data for individual experiments (2 separate donors) are given as $pIC_{50}$ (log molar inhibitory concentration of each drug which blocks aggregation to arachidonic acid by 50%) Inhibitors were preincubated for 1 minute prior to addition of arachidonic acid (200–400 μM). Changes in light transmission were measured as an index of aggregation and quantified after 4 minutes.

These properties are summarized in Tables 1 and 2 below:

| (R)-3,4-dihydroxy-5-[(all-Z)-3,6,9,12-octadecatetraenyl]-2(5H)-furanone (μM) | | |
|---|---|---|
| | | −1xLOG(0.000001xDATA) |
| RAW DATA | | |
| 764.500 | | 3.117 |
| 538.000 | | 3.269 |
| 657.000 | | 3.182 |
| 653.167 | AVE | 3.189 |
| 113.299 | STD | 0.077 |
| 65.413 | SEM | 0.044 |
| 17.346 | C V | 2.400 |
| 3 | N | 3 |
| 371.695 | −95% CL | 2.999 |
| 934.639 | +95% CL | 3.380 |
| Back-transformed/ data: (Geometric mean) | | |
| 646.510 | AVE | |
| 417.291 | −95% CL | |
| 1001.640 | +95% CL | |

TABLE 2

| (S)-3,4-Dihydroxy-5[(all-Z)-3,6,9,12-octadecatetraenyl]-2(5H)-furanone (μM) | | |
|---|---|---|
| | | −1xLOG(0.000001xDATA) |
| RAW DATA | | |
| 0.319 | | 6.496 |
| 4.300 | | 5.367 |
| 2.200 | | 5.658 |
| 2.273 | AVE | 5.840 |
| 1.992 | STD | 0.587 |
| 1.150 | SEM | 0.339 |
| 87.616 | C V | 10.043 |
| 3 | N | 3 |
| −2.675 | −95% CL | 4.383 |
| 7.221 | +95% CL | 7.297 |
| Back-transformed / data: (Geometric mean) | | |
| 1.445 | AVE | |
| 0.050 | −95% CL | |
| 41.405 | +95% CL | |

Additionally, testing in standardized screens that examine a wide-spectrum of human monocyte activities indicates that the compounds of this invention possess a spectrum of activity which makes them useful in the treatment of pathologies involving acute and chronic inflammation. These assays are as described below and Table 3 below indicate the results of testing in these assays for the compound respectively.

ASSAY: TUMOR NECROSIS FACTOR-α (TNFα)

This assay determines the effect of test compounds on the production of TNFα from purified human monocytes. Compounds are tested for their ability to downregulate the production of TNFα in activated monocytes, or upregulate secretion of TNFα in unstimulated monocytes. Test compounds are incubated for sixteen hours with purified human monocytes at four dilutions over a range of three $\log_{10}$ concentrations. Where appropriate, lipopolysaccharide (LPS) is used to stimulate the monocytes.

The level of TNFα in the resultant supernatants is quantitated in a solid phase Enzyme-linked Immunoassay (EIA) performed in a 96 well format. TNFα present in the samples is captured by a specific monoclonal antibody immobilized on the well, and detected with an anti-TNFα polyclonal antibody conjugated to horse radish peroxidase, followed by an appropriate substrate. The levels of TNFα are determined by interpolation of the resultant color change in the substrate from a standard curve. All supernatants are tested in duplicate with controls and standards.

ASSAY: INTERLEUKIN-1β (IL-1β)

This assay determines the effect of test compounds on the secretion of IL-1β from purified human monocytes.

Compounds are tested for their ability to downregulate the production of IL-1β in activated monocytes, or upregulate secretion of IL-1β in unstimulated monocytes. Test compounds are incubated for sixteen hours with purified human monocytes at four dilutions over a range of three $\log_{10}$ concentrations. Where appropriate, lipopolysaccharide (LPS) is used to stimulate the monocytes.

The level of IL-1β in the resultant supernatants is quantitated in a solid phase Enzyme-linked Immunoassay (EIA) performed in a 96 well format. IL-1β present in the samples is captured by a specific monoclonal antibody immobilized on the well, and probed with an anti-IL-1β polyclonal antibody conjugated to horseradish peroxidase, followed by an appropriate substrate. The levels of IL-1β are determined by interpolation of the resultant color change in the substrate from a standard curve. All supernatants are tested in duplicate with controls and standards.

ASSAY: INTERLEUKIN-6 (IL-6)

This assay determines the effect of test compounds on the secretion of IL-6 from purified human monocytes. Compounds are tested for their ability to downregulate the production of IL-6 in activated monocytes, or upregulate secretion of IL-6 in unstimulated monocytes. Test compounds are incubated for sixteen hours with purified human monocytes at four dilutions over a range of three $\log_{10}$ concentrations. Where appropriate, lipopolysaccharide (LPS) is used to stimulate the monocytes.

The level of IL-6 in the resultant supernatants is quantitated in a solid phase Enzyme-linked Immunoassay (EIA) performed in a 96 well format. IL-6 present in the samples is captured by a specific monoclonal antibody immobilized on the well, and probed with an anti-IL-6 polyclonal antibody conjugated to horseradish peroxidase, followed by an appropriate substrate. The levels of IL-6 are determined by interpolation of the resultant color change in the substrate from a standard curve. All supernatants are tested in duplicate with controls and standards.

ASSAY: INTERLEUKIN-8 (IL-8)

This assay determines the effect of test compounds on the secretion of IL-8 from purified human monocytes. Compounds are tested for their ability to downregulate the production of IL-8 in activated monocytes, or upregulate secretion of IL-8 in unstimulated monocytes. Test compounds are incubated for sixteen hours with purified human monocytes at four dilutions over a range of three $\log_{10}$ concentrations. Where appropriate, lipopolysaccharide (LPS) is used to stimulate the monocytes.

The level of IL-8 in the resultant supernatants is quantitated in a solid phase Enzyme-linked Immunoassay (EIA) performed in a 96 well format. IL-8 present in the samples is captured by a specific monoclonal antibody immobilized on the well, and probed with an anti-IL-8 polyclonal antibody conjugated to horseradish peroxidase, followed by an appropriate substrate. The levels of IL-8 are determined by interpolation of the resultant color change in the substrate from a standard curve. All supernatants are tested in duplicate with controls and standards.

ASSAY: GRANULOCYTE MACROPHAGE COLONY STIMULATING FACTOR (GM-CSF)

This assay determines the effect of test compounds on the expression of GM-CSF from purified human monocytes. Compounds are tested for their ability to downregulate the production of GM-CSF in activated monocytes, or upregulate secretion of GM-CSF in unstimulated monocytes. Test compounds are incubated for sixteen hours with purified human monocytes at four dilutions over a range of three $\log_{10}$ concentrations. Where appropriate, lipopolysaccharide (LPS) is used to stimulate the monocytes.

The level of GM-CSF in the resultant supernatants is quantitated in a solid phase Enzyme-linked Immunoassay (EIA) performed in a 96 well format. GM-CSF present in the samples is captured by a specific monoclonal antibody immobilized on the well, and probed with an anti-GM-CSF polyclonal antibody conjugated to horseradish peroxidase, followed by an appropriate substrate. The levels of GM-CSF are determined by interpolation of the resultant color change in the substrate from a standard curve. All supernatants are tested in duplicate with controls and standards.

ASSAY: INTERLEUKIN-1 receptor antagonist (IL-1ra)

This assay determines the effect of test compounds on the secretion of IL-1ra from purified human monocytes. Compounds are tested for their ability to downregulate or upregulate the production of IL-1ra in unstimulated monocytes and in activated monocytes. Test compounds are incubated for sixteen hours with purified human monocytes at four dilutions over a range of three $\log_{10}$ concentrations. Where appropriate, lipopolysaccharide (LPS) is used to stimulate the monocytes.

The level of IL-1ra in the resultant supernatants is quantitated in a solid phase Enzyme-linked Immunoassay (EIA) performed in a 96 well format. IL-1ra present in the samples is captured by a specific monoclonal antibody immobilized on the well, and probed with an anti-IL-1ra polyclonal antibody. A second antibody conjugated to horseradish peroxidase is then added, followed by an appropriate substrate. The levels of IL-1ra are determined by interpolation of the resultant color change in the substrate from a standard curve. All supernatants are tested in duplicate with controls and standards.

ASSAY: TISSUE FACTOR (TF)

This assay determines the effect of test compounds on the production of membrane bound tissue factor (TF) from purified human monocytes. Compounds are tested for their ability to downregulate the production of TF in activated monocytes, or upregulate production of TF in unstimulated monocytes. Test compounds are incubated for sixteen hours with purified human monocytes at four dilutions over a range of three $\log_{10}$ concentrations. Where appropriate, lipopolysaccharide (LPS) is used to stimulate the monocytes.

After the above period of incubation, medium is aspirated from the monocytes, and the cells are solubilized in Triton-X 100. The level of TF in the soluble fraction is quantitated in a solid phase Enzyme-linked Immunoassay (EIA) performed in a 96 well format. TF present in the samples is captured by a specific monoclonal antibody immobilized on the well, and detected using a biotinylated antibody fragment specific for bound TF, followed by streptavidin conjugated to horseradish peroxidase and an appropriate substrate. The levels of TF are determined by interpolation of the resultant color change in the substrate from a standard curve. All supernatants are tested in duplicate with controls and standards.

ASSAY: LEUKOTIENE $B_4$ ($LTB_4$)

This assay measures the ability of test compounds to modulate the amount of $LTB_4$ produced by the oxygenation of arachidonic acid by 5-lipooxygenase produced by purified human monocytes. Compounds are tested for their ability to downregulate the secretion of $LTB_4$ from activated monocytes, or upregulate secretion of $LTB_4$ from unstimulated monocytes. Test compounds are incubated for ninety minutes with purified human monocytes at four dilutions over a range of three $\log_{10}$ concentrations. Where appropriate, zymosan is used to stimulate the monocytes.

The level of $LTB_4$ in the resultant supernatants is quantitated by immunoassay performed in a 96 well format. $LTB_4$ levels modulated by unknown compounds are determined by interpolation from a standard curve. All compounds are tested in duplicate with controls and standards.

ASSAY: PLATELET ACTIVATING FACTOR (PAF)

This assay measures the ability of test compounds to modulate the amount of PAF produced by purified human monocytes. Compounds are tested for their ability to downregulate the secretion of PAF from activated monocytes, or upregulate secretion of PAF from unstimulated monocytes. Test compounds are incubated for ninety minutes with purified human monocytes ar four dilutions over a range of three $\log_{10}$ concentrations. Where appropriate, zymosan is used to stimulate the monocytes.

The level of PAF in the resultant supernatants is quantitated by immunoassay performed in a 96 well format. PAF levels modulated by unknown compounds are determined by interpolation from a standard curve. All compounds are tested in duplicate with controls and standards.

ASSAY: PROSTAGLANDIN $E_2$ ($PGE_2$)

This procedure measures the ability of test compounds to modulate the amount of $PGE_2$ produced by purified human monocytes. Compounds are tested for their ability to downregulate the secretion of $PGE_2$ from activated monocytes, or upregulate secretion of $PGE_2$ from unstimulated monocytes. Test compounds are incubated for ninety minutes with purified human monocytes at four dilutions over a range of three $\log_{10}$ concentrations. Where appropriate, zymosan is used to stimulate the monocytes.

The level of $PGE_2$ in the resultant supernatants is quantitated by immunoassay performed in a 96 well format. $PGE_2$ levels modulated by unknown compounds are determined by interpolation from a standard curve. All compounds are tested in duplicate with controls and standards.

ASSAY: THROMBOXANE $A_2$ ($TxA_2$)

This procedure measures the ability of test compounds to modulate the amount of $TxA_2$ (the major cyclo-oxygenase product) produced by purified human monocytes. Compounds are tested for their ability to downregulate the secretion of $TxA_2$ from activated monocytes, or upregulate secretion of $TxA_2$ from unstimulated monocytes. Test compounds are incubated for ninety minutes with purified human monocytes at four dilutions over a range of three $\log_{10}$ concentrations. Where appropriate, zymosan is used to stimulate the monocytes.

The level of $TxA_2$ in the resultant supernatants is quantitated by immunoassay performed in a 96 well format. $TxA_2$ levels modulated by unknown compounds are determined by interpolation from a standard curve. All compounds are tested in duplicate with controls and standards.

ASSAY: PEPTIDOLEUKOTRIENES

This procedure measures the ability of test compounds to modulate the amount of peptidoleukotrienes produced by purified human monocytes. Compounds are tested for their ability to downregulate the secretion of peptidoleukotrienes from activated monocytes, or upregulate secretion of peptidoleukotrienes from unstimulated monocytes. Test compounds are incubated for ninety minutes with purified human monocytes at four dilutions over a range of three $\log_{10}$ concentrations. Where appropriate, zymosan is used to stimulate the monocytes.

The level of peptidoleukotrienes in the resultant supernatants is quantitated by immunoassay performed in a 96 well format. Peptidoleukotriene levels modulated by unknown compounds are determined by interpolation from a standard curve. All compounds are tested in duplicate with controls and standards.

ASSAY: PHOSPHOLIPASE $A_2$ ($PLA_2$)

This assay measures the ability of test compounds to modulate the activity of the cellular phospholipase $A_2$ in human monocytes. Compounds are tested for their ability to inhibit stimulate phospholipase $A_2$ activity or activate basal activity in unstimulated monocytes. Test compounds are incubated for ninety minutes with purified human monocytes at four dilutions over a range of three $\log_{10}$ concentrations. Where appropriate, zymosan is used to stimulate the monocytes.

Monocytes with the arachidonyl moiety of phospholipids radiolabelled are utilized in a 96 well format. Percent release of radiolabelled fatty acid into the extracellular medium is quantified by liquid scintillation counting. All compounds are tested in duplicate with controls and standards.

ASSAY: CHEMOTAXIS

This assay measures the ability of test compounds to modulate the chemotactic response of purified human monocytes in response to a chemoattractant. Compounds are tested at four dilutions over a range of three $\log_{10}$ concentrations. The test compounds are combined with monocytes labeled with a fluorescent indicator and placed in the top wells of a chemotaxis chamber, above an optimized concentration of a monocyte chemoattractant placed in the wells below, and separated by a microporous filter. After sixty minutes, the migration of cells through the filter is quantified flurorometrically, and expressed in relation to spontaneous and maximum controls. All tests are carried out in triplicate.

ASSAY: CELL ADHESION

This assays measures the ability of test compounds to modulate adhesion of purified human monocytes to human umbilical vein endothelial cell (HUVEC) cultures. HUVECs are cultured to confluence in 96-well plates. Purified human monocytes are labelled with fluorescent dye. Triplicate cultures of HUVECs and monocytes are treated with four dilutions of test compound over a range of three $\log_{10}$ concentrations, in addition to stimulated and unstimulated controls. One hour after treatment, TNFα is added to HUVEC cultures to stimulate production of adhesion molecules. After a twelve hour incubation, the treated monocytes are added to their corresponding HUVEC cultures and incubated for ten minutes. The stimulation index (S.I.) is determined by comparing the fluorescence of treated cultures to untreated controls using a fluorometric readout in a 96-well format.

ASSAY: SUPEROXIDE ANION RELEASE

This assay measures the ability of the test compound to modulate the ability of purified human monocytes to release superoxide anions in response to a zymosan. Compounds are tested at four dilutions over a range of three $\log_{10}$ concentrations. Monocyte-compound cultures are treated with zymosan to stimulate anion production. The amount of superoxide anion produced is determined by the culture's ability to reduce cytochrome C, as measured colorimetrically. The assay is carried out in a 96-well format in triplicate and results are expressed in relation to baseline unstimulated and maximum controls. Appropriate reference controls are run with each assay.

ASSAY: MITOGEN-STIMULATED CELL PROLIFERATION and MIXED LYMPHOCYTE REACTION

The purpose of this procedure is to determine the effect of test compounds on Mixed Lymphocyte Reaction and Mitogen-Induced Proliferation of normal human mononuclear cells.

Procedure for Cell Proliferation: Peripheral blood mononuclear cells (PBMNC) are added to a 96-well cell culture plate. Compounds are tested at four dilutions, in quadruplicates, over a range of three $\log_{10}$ concentrations along with negative an inhibitory controls. The test compounds are incubated with the cells for one hour, phytohemagglutinin (PHA) is then added to all reactive test wells and the cultures are incubated for three days. The cultures are then pulsed with $^3$H incorporation is then determined with a Wallac Betaplate counter.

Procedure for Two Way Mixed Lymphocyte Reaction: PBMNC from two different donors are added to a 96-well cell culture plate. Four dilutions of test compounds, over a range of three $\log_{10}$ in quadruplicate, along with negative and inhibitory controls are then added to the plate and incubated for six days. Cultures are subsequently pulsed, harvested, and counted as above.

When tested in the above standardized assays, a representative compound of Formula I, i.e., (S)-3,4-Dihydroxy-5-[(Z)-3-octadecenyl]-2(5H)-furanone, was found to give the following results shown below in Table 3.

TABLE 3

COMPOUND:
(S)-3,4-dihydroxy-5-[(Z)-3-octadecenyl]-2-(5H)-furanone

| ASSAY | STATUS | EFFECT | UNITS: μm | EC$_{50}$ |
|---|---|---|---|---|
| TNFα | STIMULATED | STIM | | 38.0 |
| TNFα | UNSTIMULATED | NE | | |
| IL1β | STIMULATED | INHIB | IC40 [50] | |
| IL1β | UNSTIMULATED | NE | | |
| ILlra | STIMULATED | NE | | |
| ILlra | UNSTIMULATED | NE | | |
| IL6 | STIMULATED | NE | | |
| IL6 | UNSTIMULATED | NE | | |
| IL8 | STIMULATED | NE | | |
| IL8 | UNSTIMULATED | NE | | |
| GMCSF | STIMULATED | NE | | |
| GMCSF | UNSTIMULATED | NE | | |
| TISSUE FACTOR | STIMULATED | STIM | | 35.0 |
| TISSUE | UNSTIMULATED | NE | | |

TABLE 3-continued

COMPOUND:
(S)-3,4-dihydroxy-5-[(Z)-3-octadecenyl]-2-(5H)-furanone

| FACTOR | | | |
|---|---|---|---|
| SUPEROXIDE | | IA | |
| PGE2 | STIMULATED | INHIB | 2.0 |
| PGE2 | UNSTIMULATED | NE | |
| TxA2 | STIMULATED | INHIB | 5.0 |
| TxA2 | UNSTIMULATED | NE | |
| LTB4 | STIMULATED | NE | |
| LTB4 | UNSTIMULATED | NE | |
| PEPTIDOLE-UKOTRIENES | STIMULATED | NE | |
| PEPTIDOLE-UKOTRIENES | UNSTIMULATED | NE | |
| PAF | STIMULATED | NE | |
| PAF | UNSTIMULATED | NE | |
| PLA2 | STIMULATED | NE | |
| PLA2 | UNSTIMULATED | NE | |
| CHEMOTAXIS | STIMULATED | NE | |
| ADHESION | STIMULATED | NE | |
| MLR | | NE | |
| PHA | | NE | |
| MTS | | TC | 50.0 |
| LDH | | TC | 50.0 |

KEY:
NE    No effect
INHIB  Inhibition
STIM   Stimulation
IC$_{40}$   40% Inhibitory Concentration
EC$_{50}$   50% Effective Concentration
TC    Tolerated Concentration
IA    Interferes with Assay The ability of the compounds of formula I to inhibit the action of various inflammatory cytokines make them useful in a wide variety of therapeutic methods. Specifically, their ability to mediate or inhibit the actions of TNF-α makes these compounds useful in the treatment of various invasive diseases, infections, and inflammatory states. Particularly important is the inhibition of the large amount of TNF produced during serious bacterial infections, which can trigger a state of shock and tissue injury (septic shock syndrome).

A further important use of the compounds of formula I is to inhibit the TNF which is known to mediate cachexia produced during chronic disease states. Thus, these compounds are particularly useful in adjunctive therapy for AIDS and cancer patients to reduce and/or ameliorate the consequences of cachexia produced during these chronic disease states.

A further specific method of treatment for which the compounds of the instant invention are particularly useful is in the treatment of rheumatoid arthritis wherein increased amounts of the inflammatory cytokines, TNF-α and IL-1 are present. By virtue of their ability to mediate and/or inhibit the action of these cytokines, inflammation and the severity of the disease state can be reduced or eliminated.

The compounds of the instant invention can also be utilized in the treatment of multiple sclerosis (MS), Crohn's disease and ulcerative colitis by inhibiting and the activity of the inflammatory cytokines which underlie these disease states.

ASSAY: TUMOR NECROSIS FACTOR-α (TNFα)

This assay determines the effect of test compounds on the production of TNF from purified human monocytes. Compounds are tested for their ability to downregulate the production of TNFα in activated monocytes, or upregulate secretion of TNFα in unstimulated monocytes. Test compounds are incubated for sixteeen hours with purified human monocytes at four dilutions over a range of three $\log_{10}$ concentrations. Where appropriate, lipopolysaccharide (LPS) is used to stimulate the monocytes.

The level of TNFα in the resultant supernatants is quantitated in a solid phase Enzyme-linked Immunoassay (EIA) performed in a 96 well format. TNFα present in the samples is captured by a specific monoclonal antibody immobilized on the well, and detected with an anti-TNFα polyclonal antibody conjugated to horse radish peroxidase, followed by an appropriate substrate. The levels of TNFα are determined by interpolation of the resultant color change in the substrate from a standard curve. All supernatants are tested in duplicate with controls and standards.

ASSAY: INTERLEUKIN-1β (IL-1β)

This assay determines the effect of test compounds on the secretion of IL-1β from purified human monocytes. Compounds are tested for their ability to downregulate the production of IL-1β in activated monocytes, or upregulate secretion of IL-1β in unstimulated monocytes. Test compounds are incubated for sixteen hours with purified human monocytes at four dilutions over a range of three $\log_{10}$ concentrations. Where appropriate, lipopolysaccharide (LPS) is used to stimulate the monocytes.

The level of IL-1β in the resultant supernatants is quantitated in a solid phase Enzyme-linked Immunoassay (EIA) performed in a 96 well format. IL-1β present in the samples is captured by a specific monoclonal antibody immobilized on the well, and probed with an anti-IL-1β polyclonal antibody conjugated to horseradish peroxidase, followed by an appropriate substrate. The levels of IL-1β are determined by interpolation of the resultant color change in the substrate from a standard curve. All supernatants are tested in duplicate with controls and standards.

ASSAY: INTERLEUKIN-6 (IL-6)

This assay determines the effect of test compounds on the secretion of IL-6 from purified human monocytes. Compounds are tested for their ability to downregulate the production of IL-6 in activated monocytes, or upregulate secretion of IL-6 in unstimulated monocytes. Test compounds are incubated for sixteen hours with purified human monocytes at four dilutions over a range of three $\log_{10}$ concentrations. Where appropriate, lipopolysaccharide (LPS) is used to stimulate the monocytes.

The level of IL-6 in the resultant supernatants is quantitated in a solid phase Enzyme-linked Immunoassay (EIA) performed in a 96 well format. IL-6 present in the samples is captured by a specific monoclonal antibody immobilized on the well, and probed with an anti-IL-6 polyclonal antibody conjugated to horseradish peroxidase, followed by an appropriate substrate. The levels of IL-6 are determined by interpolation of the resultant color change in the substrate from a standard curve. All supernatants are tested in duplicate with controls and standards.

ASSAY: INTERLEUKIN-8 (IL-8)

The level of GM-CSF in the resultant supernatants is quantitated in a solid phase Enzyme-linked Immunoassay (EIA) performed in a 96 well format. GM-CSF present in the samples is captured by a specific monoclonal antibody immobilized on the well, and probed with an anti-GM-CSF polyclonal antibody conjugated to horseradish peroxidase, followed by an appropriate substrate. The levels of GM-CSF are determined by interpolation of the resultant color change in the substrate from a standard curve. All supernatants are tested in duplicate with controls and standards.

ASSAY: INTERLEUKIN-1 receptor antagonist (IL-1ra)

This assay determines the effect of test compounds on the secretion of IL-1ra from purified human monocytes. Compounds are tested for their ability to downregulate or upregulate the production of IL-1ra in unstimulated monocytes and in activated monocytes. Test compounds are incubated for sixteen hours with purified human monocytes at four dilutions over a range of three $\log_{10}$ concentrations. Where appropriate, lipopolysaccharide (LPS) is used to stimulate the monocytes. The level of IL-1ra in the resultant supernatants is quantitated in a solid phase Enzyme-linked Immunoassay (EIA) performed in a 96 well format. IL-1ra present in the samples is captured by a specific monoclonal antibody immobilized on the well, and probed with an anti-IL-1ra polyclonal antibody. A second antibody conjugated to horseradish peroxidase is then added, followed by an appropriate substrate. The levels of IL-1ra are determined by interpolation of the resultant color change in the substrate from a standard curve. All supernatants are tested in duplicate with controls and standards.

ASSAY: TISSUE FACTOR (TF)

This assay determines the effect of test compounds on the production of membrane bound tissue factor (TF) from purified human monocytes. Compounds are tested for their ability to downregulate the production of TF in activated monocytes, or upregulate production of TF in unstimulated monocytes. Test compounds are incubated for sixteen hours with purified human monocytes at four dilutions over a range of three $\log_{10}$ concentrations. Where appropriate, lipopolysaccharide (LPS) is used to stimulate the monocytes.

After the above period of incubation, medium is aspirated from the monocytes, and the cells are solubilized in Triton-X 100. The level of TF in the soluble fraction is quantitated in a solid phase Enzyme-linked Immunoassay (EIA) performed in a 96 well format. TF present in the samples is captured by a specific monoclonal antibody immobilized on the well, and detected using a biotinylated antibody fragment specific for bound TF, followed by streptavidin conjugated to horseradish peroxidase and an appropriate substrate. The levels of TF are determined by interpolation of the resultant color change in the substrate from a standard curve. All supernatants are tested in duplicate with controls and standards.

ASSAY: LEUKOTIENE $B_4$ ($LTB_4$)

This assay measures the ability of test compounds to modulate the amount of $LTB_4$ produced by the oxygenation of arachidonic acid by 5-lipooxygenase produced by purified human monocytes. Compounds are tested for their ability to downregulate the secretion of $LTB_4$ from activated monocytes, or upregulate secretion of $LTB_4$ from unstimulated monocytes. Test compounds are incubated for ninety minutes with purified human monocytes at four dilutions over a range of three $\log_{10}$ concentrations. Where appropriate, zymosan is used to stimulate the monocytes.

The level of $LTB_4$ in the resultant supernatants is quantitated by immunoassay performed in a 96 well format. $LTB_4$ levels modulated by unknown compounds are determined by interpolation from a standard curve. All compounds are tested in duplicate with controls and standards.

ASSAY: PLATELET ACTIVATING FACTOR (PAF)

This assay measures the ability of test compounds to modulate the amount of PAF produced by purified, human monocytes. Compounds are tested for their ability to downregulate the secretion of PAF from activated monocytes, or upregulate secretion of PAF from unstimulated monocytes. Test compounds are incubated for ninety minutes with purified human monocytes ar four dilutions over a range of three $\log_{10}$ concentrations. Where appropriate, zymosan is used to stimulate the monocytes.

The level of PAF in the resultant supernatants is quantitated by immunoassay performed in a 96 well format. PAF levels modulated by unknown compounds are determined by interpolation from a standard curve. All compounds are tested in duplicate with controls and standards.

ASSAY: PROSTAGLANDIN $E_2$ ($PGE_2$)

This procedure measures the ability of test compounds to modulate the amount of $PGE_2$ produced by purified human monocytes. Compounds are tested for their ability to downregulate the secretion of $PGE_2$ from activated monocytes, or upregulate secretion of $PGE_2$ from unstimulated monocytes. Test compounds are incubated for ninety minutes with purified human monocytes at four dilutions over a range of three $log_{10}$ concentrations. Where appropriate, zymosan is used to stimulate the monocytes.

The level of $PGE_2$ in the resultant supernatants is quantitated by immunoassay performed in a 96 well format. $PGE_2$ levels modulated by unknown compounds are determined by interpolation from a standard curve. All compounds are tested in duplicate with controls and standards.

ASSAY: THROMBOXANE $A_2$ ($TxA_2$)

This procedure measures the ability of test compounds to modulate the amount of $TxA_2$ (the major cyclo-oxygenase product) produced by purified human monocytes. Compounds are tested for their ability to downregulate the secretion of $TxA_2$ from activated monocytes, or upregulate secretion of $TxA_2$ from unstimulated monocytes. Test compounds are incubated for ninety minutes with purified human monocytes at four dilutions over a range of three $log_{10}$ concentrations. Where appropriate, zymosan is used to stimulate the monocytes.

The level of $TxA_2$ in the resultant supernatants is quantitated by immunoassay performed in a 96 well format. $TxA_2$ levels modulated by unknown compounds are determined by interpolation from a standard curve. All compounds are tested in duplicate with controls and standards.

ASSAY: PEPTIDOLEUKOTRIENES

This procedure measures the ability of test compounds to modulate the amount of peptidoleukotrienes produced by purified human monocytes. Compounds are tested for their ability to downregulate the secretion of peptidoleukotrienes from activated monocytes, or upregulate secretion of peptidoleukotrienes from unstimulated monocytes. Test compounds are incubated for ninety minutes with purified human monocytes at four dilutions over a range of three $log_{10}$ concentrations. Where appropriate, zymosan is used to stimulate the monocytes.

The level of peptidoleukotrienes in the resultant supernatants is quantitated by immunoassay performed in a 96 well format. Peptidoleukotriene levels modulated by unknown compounds are determined by interpolation from a standard curve. All compounds are tested in duplicate with controls and standards.

ASSAY: PHOSPHOLIPASE $A_2$ ($PLA_2$)

This assay measures the ability of test compounds to modulate the activity of the cellular phospholipase $A_2$ in human monocytes. Compounds are tested for their ability to inhibit stimulate phospholipase $A_2$ activity or activate basal activity in unstimulated monocytes. Test compounds are incubated for ninety minutes with purified human monocytes at four dilutions over a range of three $log_{10}$ concentrations. Where appropriate, zymosan is used to stimulate the monocytes.

Monocytes with the arachidonyl moiety of phospholipids radiolabelled are utilized in a 96 well format. Percent release of radiolabelled fatty acid into the extracellular medium is quantified by liquid scintillation counting. All compounds are tested in duplicate with controls and standards.

ASSAY: CHEMOTAXIS

This assay measures the ability of test compounds to modulate the chemotactic response of purified human monocytes in response to a chemoattractant. Compounds are tested at four dilutions over a range of three $log_{10}$ concentrations. The test compounds are combined with monocytes labeled with a fluorescent indicator and placed in the top wells of a chemotaxis chamber, above an optimized concentration of a monocyte chemoattractant placed in the wells below, and separated by a microporous filter. After sixty minutes, the migration of cells through the filter is quantified flurorometrically, and expressed in relation to spontaneous and maximum controls. All tests are carried out in triplicate.

ASSAY: CELL ADHESION

This assays measures the ability of test compounds to modulate adhesion of purified human monocytes to human umbilical vein endothelial cell (HUVEC) cultures. HUVECs are cultured to confluence in 96-well plates. Purified human monocytes are labelled with fluorescent dye. Triplicate cultures of HUVECs and monocytes are treated with four dilutions of test compound over a range of three $log_{10}$ concentrations, in addition to stimulated and unstimulated controls. One hour after treatment, TNF$\alpha$ is added to HUVEC cultures to stimulate production of adhesion molecules. After a twelve hour incubation, the treated monocytes are added to their corresponding HUVEC cultures and incubated for ten minutes. The stimulation index (S.I.) is determined by comparing the fluorescence of treated cultures to untreated controls using a fluorometric readout in a 96-well format.

ASSAY: SUPEROXIDE ANION RELEASE

This assay measures the ability of the test compound to modulate the ability of purified human monocytes to release superoxide anions in response to a zymosan. Compounds are tested at four dilutions over a range of three $log_{10}$ concentrations. Monocyte-compound cultures are treated with zymosan to stimulate anion production. The amount of superoxide anion produced is determined by the culture's ability to reduce cytochrome C, as measured colorimetrically. The assay is carried out in a 96-well format in triplicate and results are expressed in relation to baseline unstimulated and minimum controls. Appropriate reference controls are run with each assay.

ASSAY: MITOGEN-STIMULATED CELL PROLIFERATION and MIXED LYMPHOCYTE REACTION

The purpose of this procedure is to determine the effect of test compounds on Mixed Lymphocyte Reaction and Mitogen-Induced Proliferation of normal human mononuclear cells.

Procedure for Cell Proliferation: Peripheral blood mononuclear cells (PBMNC) are added to a 96-well cell culture plate. Compounds are tested at four dilutions, in quadruplicates, over a range of three $log_{10}$ concentrations along with negative an inhibitory controls. The test compounds are incubated with, the cells for one hour, phytohemagglutinin (PHA) is then added to all reactive test wells and the cultures are incubated for thee days. The cultures are then pulsed with $^3H$ incorporation is then determined with a Wallac Betaplate counter.

Procedure for Two Way Mixed Lymphocyte Reaction: PBMNC from two different donors are added to a 96-well cell culture plate. Four dilutions of test compounds, over a range of three $log_{10}$ in quadruplicate, along with negative and inhibitory controls are then added to the plate and incubated for six days. Cultures are subsequently pulsed, harvested, and counted as above.

The compounds of the invention may be formulated in a conventional manner, optionally together with one or more other active ingredients, for administration by any convenient route for example of oral, intravenous or intramuscular administration.

Thus, according to another aspect, the invention provides a pharmaceutical composition comprising a compound of formulae Ia or Ib and/or a pharmaceutically acceptable salt thereof together with a pharmaceutically acceptable carrier or excipient.

For oral administration, the pharmaceutical composition may take the form of, for example, tablets, capsules, powders, solutions, syrups or suspensions prepared by conventional means with physiologically acceptable excipients.

The compounds may be formulated for intravenous or intramuscular administration in dry form for reconstitution before use, or as a sterile solution or suspension.

A proposed daily dose based on similar pharmacokinetic parameters to CHTA for administration to man is 10 to 25 mg/kg, for example 1 gm daily to 70 kg, which may be conveniently administered in 1 to 3 doses per day. The precise dose administered will, of course, depend on the age and condition of the patient.

The following examples illustrate the present invention.

Melting points were determined in open capillaries with a Thomas-Hoover Uni-Melt Apparatus and are uncorrected. Infrared spectra were recorded by a Laser Precision Analytical RFX-FTIR spectrometer (model TSI-400). Nuclear magnetic resonance spectra were obtained with either an IBM-Bruker model NR/256, 270 or 500 FT NMR spectrometer. Tetramethylsilane (TMS) in $CDCl_3$, acetone-$d_6$, or $CD_3OD$ was used as internal standard. Chemical shifts were reported on the $\delta$ scale with peak multiplicities: s, singlet; d, doublet; dd, doublet of doublets; ddd, doublet of doublets of doublets; t, triplet; q, quartet; m, multiplet. Tetrahydrofuran (THF) was distilled from Na/benzophenone ketyl and $CH_2Cl_2$ was dried over $P_2O_5$. Optical rotations were taken on a Perkin-Elmer model 241 polarimeter using a 10 cm, 1 Ml cell. Mass spectra were acquired with either a Kratos MS25RFA or a VG 70-250S mass spectrometer. Elemental analyses were performed by Galbraith Laboratories, Inc., Knoxville, Tenn.

PREPARATION OF STARTING MATERIALS

EXAMPLE A 3,6,9-Pentadecatriyn-1-ol.

In a 1 L three-necked, flame-dried round bottom flask fitted with a reflux condenser and a rubber septum was placed 3.86 g (159 mmol) of magnesium in 250 mL of anhydrous tetrahydrofuran. Bromoethane (17.3 g; 1586 mmol) in 250 mL anhydrous tetrahydrofuran was added dropwise, under argon, and the reflux rate was controlled with the aid of an ice-water bath. The mixture was heated to reflux and stirred for 1 hour. 3-Butyn-1-ol (5.56 g, 79.3 mmol), dissolved in 150 mL of anhydrous tetrahydrofuran, was slowly added dropwise with stirring (2 hours). Following addition, the reaction was heated to reflux. After stirring for 90 minutes, 0.5 g (2.63 mmol) of cuprous (I) iodide was added. After 75 minutes 9.0 g (39.65 mmol) of 1-bromo-2,5-undecadiyne dissolved in 150 mL of anhydrous tetrahydrofuran was added. The mixture was heated at reflux for 12 h and an additional 0.25 g (1.32 mmol) of cuprous (I) iodide was added. The mixture was heated at reflux for 7 hours, cooled and quenched by addition of 400 mL of ice-water saturated with ammonium chloride. After filtration (Celite), the filtrate was extracted with 3×400 mL of ether. The ether layers were washed with 2×300 mL of saturated ammonium chloride solution, 3×200 mL of water, 250 mL of brine, dried ($Na_2SO_4$), and concentrated in vacuo to yield 6.2 g of yellow-brown oil. The residue was partially purified by crystallization (petroleum ether) at $-20°$ C. to produce 5.75 g (75%) of an unstable yellow oil (room temperature) which was utilized immediately in the next reaction. IR (neat,$cm^{-1}$) 3365, 2956, 2933, 2225; $^1H$ NMR ($CDCl_3$) $\delta$ 3.70 (t, J=6.2 Hz, 2H), 3.17–3.13 (m, 4H), 2.45 (dt, J=1.5, 5.9, 12.0 Hz, 2H), 2.15 (dt, J=2.1, 6.9, 13.9 Hz, 2H), 1.68 (br, 1H), 1.55–1.43 (m, 2H), 1.43–1.26 (m, 4H), 0.89 (t, J=6.9 Hz, 3H); HRMS calculated for $C_{15}H_{20}O$ ($M^+$) 216.1514, found 216.1519.

(3Z,6Z,9Z)-3,6,9-Pentadecatriene-1-ol.

3,6,9-Pentadecatriynol (5.75 g, 26.6 mmol), 5% palladium on barium sulfate (0.5 g) and 5 drops of 3% quinoline in methanol were added to a 500 mL hydrogenation flask. Hydrogen, at an initial pressure of 72 psi, was taken up over 30 minutes. The mixture was filtered (Celite) and the filtrate was evaporated in vacuo to produce 5.7 g of crude triene which was purified over silica gel using ethyl acetate:hexanes (1:5) yielding 5.5. g (93%) of light yellow oil: IR (neat, $cm^{-1}$) 3336 (br), 3012, 2958, 2927, 1652, 719; $^1H$ NMR ($CDCl_3$) $\delta$ 5.60–5.28 (m, 6H), 3.67 (t, J=6.4 Hz, 2H), 2.88–2.79 (m, 2H), 2.43–2.33 (m, 2H), 2.12–1.98 (m, 2H), 1.68–1.53 (m, 2H), 1.53–1.23 (m, 6H), 0.89 (t, J=6.7 Hz, 3H); HRMS calculated for $C_{15}H_{26}O$ ($M^+$) 222.1984, found 222.1990.

(3Z,6Z,9Z)-1-Bromo-3,6,9-pentadecatriene.

To a 250 mL three-necked round bottom flask was added under nitrogen 9.46 g (36.1 mmol) of triphenylphosphine dissolved in 150 mL of anhydrous acetonitrile. After cooling to 0° C. (ice-salt bath), bromine (5.77 g, 36.1 mmol) was added dropwise with stirring. The mixture was warmed to room temperature and stirred for 30 minutes. 3,6,9-Pentadecatrienol (6.16 g, 27.75 mmol); dissolved in 50 mL of anhydrous acetonitrile, was added dropwise (15 minutes) and stirred for approximately 4 hours. Upon reaction completion acetonitrile was removed in vacuo and the residue was dissolved in 75 mL of ether. Hexanes were utilized to precipitate the triphenylphosphorane side product which was removed by filtration. The crude residue, obtained after concentration of the filtrate in vacuo, was purified over silica gel using ethyl acetate:hexanes (1:9) as eluant. The product 7.0 g (90%) was obtained as a light yellow oil. IR (neat,$cm^{-1}$) 2958, 2927, 1652, 1267, 723;$^1H$ NMR ($CDCl_3$) $\delta$ 5.69–5.28 (m, 6H), 3.38 (t, J=7.1 Hz, 2H), 2.89–2.75 (m, 4H), 2.75–2.52 (m, 2H), 2.12–1.93 (m, 2H), 1.49–1.31 (m, 6H), 0.89 (t, J=6.8 Hz, 3H); $^{13}C$ NMR ($CDCl_3$) $\delta$ 131.0, 130.6, 128.9, 127.4 (2C), 126.3, 32.2, 31.5, 30.9, 29.3, 27.3, 25.8, 25.7, 22.6, 14.0; HRMS calculated for $C_{15}H_{25}Br$ ($M^+$) 284.1139, found 284.1101.

[(3Z, 6Z, 9Z)-3,6,9,-Pentadecatrieyl]triphenylphosphonium Bromide.

Bromo-3,6,9-pentadecatriene (7.0 g, 24.6 mmol) was treated with 7.5 g (28.6 mmol) of triphenylphosphine in 25 mL of acetonitrile. The mixture was heated to 70° C. under nitrogen atmosphere. Following reaction completion (monitor salt formation by TLC; 72 hours) the mixture was dried for 36 hours under reduced pressure to ensure removal of traces of acetonitrile. The resultant yellow residue, 13.45 g, was used in the next reaction without further purification: IR (neat, $cm^{-1}$) 3010, 2958, 1652, 1191, 723; $^1H$ NMR ($CDCl_3$) $\delta$ 7.93–7.61 (m, 15 H), 5.69–5.12 (m, 6H), 4.02–3.91 (m, 2H), 2.69–2.48 (m, 4H), 2.09–1.92 (m, 2H), 1.89–1.72 (m, 2H), 1.46–1.25 (m, 6H), 0.88 (t, J=6.9 Hz, 3H).

(S)-2,2-Dimethyl-4-oxo-1,3-dioxolane-5-acetyl Chloride.

To 20 g (1149 mmol) of (S)-2,2-dimethyl-4-oxo-1,3-dioxolane -5-acetic acid in a dry 250 mL round bottom flask was added under argon and at room temperature 75 g (630 mmol) of thionyl chloride and 2 drops of DMF. The reaction mixture was stirred until evolution of gaseous Hcl ceased (oil bubbler; approximately 2 hours). The excess thionyl chloride was distilled in vacuo and remaining traces were removed under reduced pressure (9 hours). The acid chloride (22.1 g) thus obtained was utilized without further purification in the next step:

IR (neat, cm$^{-1}$) 2998, 1793, 1751, 989, 958; $^1$H NMR (CDCl$_3$) δ 4.69 (dd, J=3.6, 6.4 Hz, 1H), 3.56 (dd, J=3.6, 18.1 Hz, 1H), 3.36 (dd, J=6.4, 18.1 Hz, 1H), 1.65 (s, 3H), 1.58 (s, 3H).

(S)-2,2-Dimethyl-4-oxo-1,3-dioxolane-5-acetaldehyde.

To a 500 mL three-necked flask equipped with a mechanical stirrer, reflux condenser and gas inlet dispersion tube was added 22.1 g (115 mmol) of crude (S)-2,2-dimethyl-4-oxo-1,3-dioxolane-5-acetyl chloride dissolved in 250 mL of anhydrous xylenes. To this solution was added 2.0 g of 5% palladium on barium sulfate and 0.2 mL of stock quinoline-sulfur poison solution (prepared by refluxing 1 g of sulfur with 5 mL of quinoline for 6 hours and diluting to a final volume of 70 Ml with anhydrous xylenes). Hydrogen gas was bubbled through the stirred reaction mixture and the hydrogen chloride gas generated was trapped in 175 mL of water containing a few drops of phenolphthalein indicator. The mixture was heated at 135° C. and monitored by titration of the hydrogen chloride solution with 5M sodium hydroxide solution. On completion (approximately 3 hours), the reaction mixture was cooled to room temperature and 1.5 g of Norit was added. The mixture was filtered (Celite) and the filtrate concentrated under reduced pressure. The residue was purified over silica gel using ethyl acetate:hexanes (1:3) to furnish 16.2 g (89%) of white solid: mp 37°–38° C.; [α]$_D^{25}$1.4° (c=4.54, CH$_3$OH); IR (neat, cm$^{-1}$) 2994 2744, 1793, 1725, 1386; $^1$H NMR (CDCl$_3$) δ 9.78 (s, 1H), 4.80 (dd, J=3.6, 6.8 Hz, 1H), 3.10 (dd, J=3.6, 18.3 Hz, 1H); 2.92 (dd, J=6.9, 18.3 Hz, 1H), 1.63 (s, 3H), 1.58 (s, 3H); HRMS calculated for C$_7$H$_{10}$O$_4$ (M$^+$) 158.0579, found 158.0572.

(S)-5-(3-Methoxyallyl)-2,2-dimethyl -1,3-dioxolane-4-one.

In a dry 500 mL three-necked round bottom flask under argon was dissolved 14.2 g (126.58 mmol) of potassium t-butoxide in 300 mL of anhydrous tetrahydrofuran. The solution was cooled to 0° C. and 44 g (126.6 mmol) of methoxymethyltriphenylphosphine chloride was added slowly and with stirring (20 minutes). The resulting orange-red solution was stirred at 0° C. for 45 minutes and 10 g (63.3 mmol) of (S)-2,2-dimethyl-4-oxo-1,3-dioxolane-5-acetaldehyde in 50 mL of anhydrous tetrahydrofuran was added dropwise (15 minutes). The mixture was allowed to stir at ambient temperature for 1 hour and quenched by addition of 100 mL of brine. Following stirring for 1 hour, the mixture was extracted with 3×250 mL of ether. The combined ether extract was washed with 2×150 mL of brine, dried (Na$_2$SO$_4$) and filtered. The filtrate was evaporated under reduced pressure to yield 18 g of a crude brown colored liquid (contaminated with the triphenylphosphorane). This residue was purified over silica gel using ethyl acetate:petroleum ether (1:9) to give 9.2 g (78%) of a mixture of inseparable E:Z enol ethers as a colorless liquid: [α]$_c^{25}$–3.2° (c=2.8, CH$_3$OH); IR (neat, cm$^{-1}$) 2994, 2938, 1793, 1658; $^1$H NMR (CDCl$_3$) δfor the E-enol ether (75%) 6.42 (d, J=12.7 Hz, 1H), 4.49–4.34 (m, 2H), 3.53 (s 3H), 2.72–2.32 (m, 2H), 1.60 (s, 3H), 1.54 (s, 3H), for the Z-enol ether (25%) 6.04 (d, J=6.1 Hz, 1H), 4.78–4.61 (m, 2H), 3.61 (s, 3H), 2.72–2.32 (m, 2H), 1.60 (s, 3H), 1.54 (s, 3H); HRMS calculated for C$_9$H$_{14}$O$_4$ (M$^+$) 186.0892, found 186.0894.

Methyl (2S)-Tetrahydro-5-methoxy-2-furoate.

To the enol ethers, (S)-5-(3-methoxyallyl)-2,2-dimethyl-1,3-dioxolan-4-one (4.0 g, 21.5 mmol), dissolved in 150 mL of anhydrous methanol was added 5–6 drops of concentrated H$_2$SO$_4$. The resultant solution was heated for 6 hours and cooled to room temperature. Sodium bicarbonate (0.5 g) was added, and the methanol was removed in vacuo. The residue was dissolved in 250 mL of CH$_2$Cl$_2$ and washed with 2×100 mL of saturated sodium bicarbonate solution and 2×125 mL of brine. The organic extract was dried (Na$_2$SO$_4$) and the solvent removed under reduced pressure to produce a colorless liquid which was purified over silica gel using ethyl acetate:hexanes (1:1) as eluant to provide 2.93 g (86%) of a colorless liquid as a 3:1 mixture of diastereomers: [α]$_D^{25}$ 27.3° (c=1.2, CH$_3$OH); IR (neat, cm$^{-1}$) 2958, 1739, 1213, 1105; $^1$H NMR (CDCl$_3$) δ for diastereomer A (66%) 5.21 (m, 1H), 4.64–4.52 (m, 1H), 3.77 (s, 3H), 2.44–1.83 (m, 4H); for diastereomer B (33%) 5.08 (m, 1H), 4.64–4.52 (m, 1H), 3.77 (s, 3H), 3.42 (s, 3H), 2.44–1.83 (m, 4H); HRMS calculated for C$_7$H$_{12}$O$_4$ (M$^+$) 160.0735, found 160.0718.

Methyl (2S)-Tetrahydro-5-hydroxy-2-furoate.

Methyl (2S)-tetrahydro-5-methoxy-2-furoate (2.93 g, 18.3 mmol) was stirred with 500 mL of 25% aqueous acetic acid for approximately 10 hours (monitor by TLC). Upon reaction completion the aqueous acetic acid was removed in vacuo and the residue was purified over silica gel using ethyl acetate:hexane (1:1) to give 2.4 g (90%) of a colorless liquid as a 5.8:4.2 diastereomeric mixture: [α]$_D^{25}$ 9.3° (C=2.7, CH$_3$OH); IR (neat, cm$^{-1}$) 3457 (br), 2956, 1735, 1062, 1010; $^1$H NMR (CDCl$_3$) δ for diastereomer A (58%) 5.62 (m, 1H), 4.60 (dd, J=6.5, 8.1 Hz, 1H), 3.78 (s, 3H), 2.46–1.93 (m, 4H); for diastereomer B (42%) 5.75 (m, 1H), 4.73 (dd, J=3.8, 8.5 Hz, 1H), 3.76, (s, 3H), 2.46–1.93 (m, 4H); HRMS calculated for C$_6$H$_{10}$O$_4$ (M$^+$) 146.0579, found 146.0574.

Methyl (S)-2-Hydroxyarachiodonate.

To a flame-dried, 500 mL three-necked flask, fitted with a low temperature thermometer and a rubber septum, was added under argon 12.35 g (22.57 mmol) of 3,6,9-pentadecatrienetriphenyl-phosphine bromide and 350 mL of anhydrous tetrahydrofuran. The solution was cooled to –35° C. and 14.1 mL of 1.6 M n-BuLi in hexanes (22.56 mmol) was added dropwise with stirring. The dark red solution was warmed to room temperature, stirred for an additional 30 minutes and cooled to –35° C. The solution was cooled to –60° C., and methyl (2S)-tetrahydro-5-hydroxy-2-furoate (1.65 g, 11.28 mmol) dissolved in 25 mL of anhydrous tetrahydrofuran was added dropwise (approximately 15 minutes). The mixture was stirred at –60° C. for 2 hours and warmed to room temperature. Upon completion (TLC monitoring, approximately 8–9 hours), the reaction was quenched by the addition of 100 mL of 10% aqueous Hcl solution and extracted with 3×300 mL of ethyl acetate. The organic layers were washed with 3×250 mL of water, 2×200 mL of brine, dried (Na$_2$SO$_4$), filtered and concentrated in vacuo. The residue contaminated with the triphe. nylphosphorane, was purified over silica gel using ethyl acetate:hexanes (1:5) as eluant to provide 3.1 g (82%) of yellow oil: [α]$_D^{25}$ 10.2° (c=5.4,CH$_3$OH); IR (neat, cm$^{-1}$) 3477 (br), 3012, 2956, 1739, 1652, 721; $^1$H NMR (CDCl$_3$) δ 5.45–5.25 (m, 8H), 4.20 (dd, J=4.0, 7.6 Hz, 1H), 3.79 (s, 3H), 2.92–2.74 (m, 4H), 2.35–1.92 (m, 4H), 1.91–1.62 (m, 2H), 1.49–1.24 (m, 6H), 0.89 (t, J=6.4 Hz, 3H); HRMS calculated for C$_{21}$H$_{34}$O$_3$(M$^+$) 334.2507, found 334.2509; analysis calculated for C$_{21}$H$_{34}$O$_3$: C, 75.41; H, 10.25. Found C, 75.36; H, 10.13.

EXAMPLE B (R)-2,2-Dimethyl-4-oxo-1,3-dioxolane-5-acetyl Chloride was prepared as for the S-isomer of Example A from R-malic acid in similar yield: IR (neat, cm$^{-1}$) 2996, 1793, 1751, 989 958; $^1$H NMR (CDCl$_3$) δ 4.69 (dd, J=3.6, 6.4 Hz, 1H), 3.53 (dd, J=3.6, 18.1 Hz, 1H) 3.35 (dd, J=6.4, 18.1 Hz, 1H) 1.65 (s, 3H), 1.58 (s, 3H).

(R)-2,2-Dimethyl-4-oxo-1,3-dioxolane-5-acetaldehyde was prepared as for the S-isomer from (R)-2,2-dimethyl-4-oxo-1,3-dioxolane-5-acetyl chloride in similar yield: mp 37°–38° C.; [α]$_D^{25}$ 3.7° (c=5.12, CH$_3$OH); IR (neat, cm$^{-1}$) 2996, 2746, 1791, 1727, 1388; ¨H NMR (CDCl$_3$) δ 9.78 (s, 1H), 4.80 (dd, J=3.6, 6.8 Hz, 1H), 3.11 (dd, J=3.6, 18.3 Hz, 1H), 2.93 (dd, J=6.9, 18.3 Hz, 1H), 1.63 (s, 3H), 1.58 (s, 3H); HRMS calculated for C$_7$H$_{10}$O$_4$ (M$^+$) 158.0579, found 158.0574.

5(R)-5-(3-Methoxyallyl)-2,2-dimethyl-1,3-dioxolan-4-one was prepared as for the S-isomer from (R)-2,2-dimethyl-5-oxo-1,3-dioxolane-4-acetaldehyde in similar yield: [α]$_D^{25}$ 3.1° (c=3.07, CH$_3$OH); IR (neat, cm$^{-1}$) 2992, 2740, 1793, 1656; $^1$H NMR (CDCl$_3$) for the E-enol ether (72%) δ 6.42 (d, J=12.7 Hz, 1H), 4.49–4.34 (m, 2H), 3.53 (s, 3H), 2.72–2.32 (m, 2H), 1.61 (s, 3H), 1.54 (s, 3H); for the Z-enol ether (28%) 6.05 (d, J=6.1 Hz, 1H), 4.78–4.65 (m, 2H), 3.61 (S, 3H), 2.72–2.32 (m, 2H), 1.61 (S, 3H), 1.54 (S, 3H); HRMS calculated for C$_9$H$_{14}$O$_4$(M$^+$) 186.0892, found 186.0891.

Methyl (2R)-Tetrahydro-5-methoxy-2-furoate was prepared as for the S-isomer from (R)-5-(3-methoxyallyl)-2,2-dimethyl-1,3-dioxolane-4-one in similar yield: [α]$_D^{25}$ −28.33° (c=0.1, CH$_3$OH); IR (neat, cm$^{-1}$) 2956, 1754, 1209, 1105; $^1$H NMR (CDCl$_3$) diastereomer A (66%) δ 5.21 (m, 1H), 4.64–4.52 (m, 1H), 3.77 (s, 3H), 3.38 (s, 3H), 2.42–1.84 (m, 4H) for diastereomer B (33%) 5.08 (m, 1H), 4.64–4.52 (m, 1H), 3.77 (s, 3H), 3.42 (s, 3H), 2.42–1.84 (m, 4H); HRMS calculated for C$_7$H$_{12}$O$_4$ (M$^+$) 160.0735, found 160.0750.

Methyl (2R)-Tetrahydro-5-hydroxy-2-furoate was prepared as for the S-isomer from methyl (2R)-tetrahydro-5-methoxy-2-furoate in similar yield: [α]$_D^{25}$ −9.2° (c=1.8, CH$_3$OH); IR (neat, cm$^{-1}$) 3543 (br), 2956, 1741, 1068, 1010; $^1$H NMR (CDCL$_3$) for diastereomer A (58%) δ 5.62 (m, 1H), 4.67 (dd, J=6.5, 8.1 Hz, 1H), 3.78 (s, 3H), 2.46–1.93 (m, 4H); for diastereomer B (42%) δ 5.75 (m, 1H), 4.73 (dd, J=3.8, 8.5 Hz, 1H), 3.76 (s, 3H), 2.46–1.93 (m, 4H); HRMS calculated for C$_6$H$_{10}$O$_4$ (M$^+$), 146.0579, found 146.0577.

Methyl (R)-2-Hydroxyarachidonate was prepared as for the S-isomer from methyl (2R)-tetrahydro-5-hydroxy-2-furoate in similar yield: [α]$_D^{25}$ −10.5° (c=0.9, CH$_3$OH); IR (neat, cm$^{-1}$) 3504 (br), 3012, 2956, 1739, 1652, 723; $^1$H NMR (CDCL$_3$) δ 5.45–5.25 (m, 8H), 4.20 (dd, J=4.0, 7.7 Hz, 1H), 3.79 (s, 3H), 2.92–2.74 (m, 4H); 1.90–1.62 (m, 2H), 1.49–1.24 (m, 6H), 0.89 (t, J=6.4 Hz, 3H), HRMS calculated for C$_{21}$H$_{34}$O$_3$(M$^+$), 334.2507, found 334.2506.

EXAMPLE C

Pentadecyltriphenylphosphonium Bromide.

Under nitrogen atmosphere 1-bromopentadecane (6.5 g, 22.4 mmol) was treated with 5.87 g (22.4 mmol) of triphenylphosphine in 15 mL of acetonitrile and heated to 135° C. The reaction was monitored by TLC (salt formation, about 18 hours), and the mixture was dried under reduced pressure (24 hours) to ensure removal of traces of acetonitrile and provided 12.3 g of a colorless solid which was utilized in the next reaction without further purification. Methyl (2S,5Z)-2-Hydroxy-5-eicosenoate.

To a flame-dried 500 mL three-necked flask fitted with a low temperature thermometer and a rubber septum, was added under argon 12.2 g (22.06 mmol) of pentadecyltriphenylphosphonium bromide and 300 mL of anhydrous tetrahydrofuran. Following cooling to −35° C., 13.8 mL of 1.6 M n-BuLi in hexanes (22.06 mmol) was added dropwise and with stirring. The orange solution was warmed to room temperature and stirred for an additional 30 minutes. The mixture was cooled to −35° C., and 18.5 g (103.3 mmol) of hexamethylphosphoramide was added slowly. The reaction mixture was stirred for 45 minutes and cooled to −60° C. Methyl (2S)-tetrahydro-5-hydroxy-2-furoate (1.6 g, 11.03 mmol) and dissolved in 25 mL of anhydrous tetrahydrofuran was added dropwise, and stirring was continued for 1 hour at −60° C. The mixture was warmed to room temperature; reaction completion was monitored using TLC. The reaction was quenched by addition of 100 mL of 10% aqueous Hcl solution and extracted with 3×300 mL of ethyl acetate. The organic layers were washed with 3×250 mL of water, 2×200 mL of brine, dried (Na$_2$SO$_4$), filtered and evaporated in vacuo. The residue, contaminated with triphenylphosphorane, was purified over silica gel using ethyl acetate:hexanes (1:5) to yield 2.98 g (80%) of colorless oil: [α]$_D^{25}$ +8.9° (c=1.4, CH$_3$OH); IR neat, cm$^{-1}$) 3475 (br), 3006, 2925, 1739, 721; $^1$H NMR (CD$_3$COCD$_3$) δ 5.48–5.24 (m, 2H), 4.20 (m, 1H), 3.79 (s, 3H), 2.72 (d, J=5.3 Hz, 1H), 2.32–2.15 (m, 2H), 2.15–1.98 (m, 2H), 1.92–1.64 (m, 2H), 1.48–1.21 (m, 24E), 0.88 (t, J=6.3 Hz, 3H); $^{13}$C NMR (CD$_3$COCD$_3$) δ 175.7, 131.5, 127.9, 70.0, 52.4, 34.4, 31.9, 29.7 (5C), 29.6 (2C), 29.3 (3C), 27.2, 22.7 (2C), 14.0; HRMS calculated for C$_{21}$H$_{40}$O$_3$ (M$^+$) 340.2977, found 340.2977; analysis calculated for C$_{21}$H$_{40}$O$_3$: C, 74.07; H, 11.84: Found: C, 74.13; H, 11.71.

EXAMPLE D

Methyl (2R, 5Z)-2-Hydroxy-5-eicosenoate was prepared as for the S-isomer from methyl (2R)-tetrahydro-5-hydroxy-2-furoate in similar yield: [α]$_D^{25}$ −8.8° (c=2.1, CH$_3$OH); IR (neat, cm$^{-1}$) 3482 (br), 3006, 2925, 1739, 721; $^1$H NMR (CD$_3$COCD$_3$) δ 5.48–5.24 (m, 2H), 4.20 (m, 1H), 3.79 (s, 3H), 2.72 (d, J=5.3 Hz, 1H), 2.32–2215 (m, 2H), 2.15–1.98 (m, 2H), 1.92–1.64 (m, 2H), 1.48–1.21 (m, 24H), 0.88 (t, J=6.3 Hz, 3H); $^{13}$C NMR (CD$_3$COCD$_3$) δ 175.7, 131.5, 127.9, 70.0, 52.3, 34.4, 31.9, 29.7 (5C), 29.6 (2C), 29.3 (3C), 27.2, 22.7 (2C), 14.0; HRMS calculated for C$_{21}$H$_{40}$O$_3$ (M$^+$) 340.2977, found 340.2970.

EXAMPLE 1

Methyl (S)-2-(Allyloxy)acetyloxy arachidinoate.

To a dry two-necked round bottom flask fitted with a rubber septum was added, under argon, 1.5 g (4.49 mmol) of methyl (S)-2-hydroxyarachidonate dissolved in 125 mL of anhydrous CH$_2$Cl$_2$. The solution was cooled to 10° C. (ice bath) and 1.30 g of allyloxyacetic acid (11.23 mmol) dissolved in 15 mL of anhydrous CH$_2$Cl$_2$ and 0.133 g (0.90 mmol) of 4-pyrrolidinopyridine dissolved in 2 mL of anhydrous CH$_2$Cl$_2$ was added. A solution of 2.32 g (11.23 mmol) of DCC in 25 mL of CH$_2$Cl$_2$ was added dropwise with stirring, warmed to room temperature, and stirred overnight. CH$_2$Cl$_2$ was removed by distillation under reduced pressure and the residue was chromatographed on silica gel using ethyl acetate:hexanes (1:5) as eluant to furnish 1.79 g (92%) of yellow oil: [α]$_D^{25}$ −8.1° (c=0.1, CH$_3$OH); IR (neat, cm$^{-1}$) 3012, 2956, 1751, 1652; $^1$H NMR (CDCl$_3$) a 5.94–5.82 (m, 1H), 5.41–5.22 (m, 10H), 5.11 (t, J=6.3 Hz, 1H), 4.23 (d, J=16.6 Hz, 1H), 4.22 (d, J=16.6 Hz, 1H), 4.12 (d, J=1.3, 5.7 Hz, 2H), 3.75 (s, 3H), 2.89–2.68 (m, 4H), 2.32–1.89 (m, 2H), 1.42–1.31 (m, 6H), 0.89 (t, 6.5 Hz, 3H); HRMS calculated for $C_{26}H_{40}O_5$ (M$^+$) 432.2875, found 432.2856; analysis calculated for $C_{26}H_{40}O_5$: C, 72.19; H, 9.32: Found: C, 71.90; H, 9.11.

(S)-3-(Allyloxy)-4-hydroxy-5-[(all-Z)-3,6,9,12-octadecatetraenyl]-2(5H)-furanone.

To a flame-dried, three-necked, 250 mL round bottom flask under argon fitted with a low temperature thermometer, and a septum was added 1.23 g (7.59 mmol) of hexamethyldisilazane in 100 mL of anhydrous tetrahydrofuran. The contents were cooled to −25° C. (dry ice, CCl$_4$) and 4.75 mL of 1.6 M (7.59 mmol) n-BuLi in hexanes was added dropwise with stirring while maintaining the temperature below −15° C. The stirred reaction mixture was warmed to −5° C., the contents maintained between −5° C. and 0° C. for 45 minutes, and cooled to −78° C. (dry ice/acetone). Methyl (S)-2-hydroxyarachidonate, (allyloxy) acetate (1.56 g, 3.61 mmol) in 30 mL of anhydrous tetrahydrofuran was added dropwise with stirring while maintaining the temperature below −68° C. Following addition, the mixture was stirred at −78° C. for 75 minutes and quenched by addition of 40 mL of 10% aqueous HCl solution. Ether (125 mL) was added, the mixture warmed to room temperature, and extracted with 3×100 mL of ether. The ether extract was washed with 2×75 mL of brine, dried (Na$_2$SO$_4$) and concentrated in vacuo to yield 1.34 g of crude product which was purified over silica gel using 10% methanol in chloroform as eluant to provide 1.28 g (89%) of yellow oil: $[\alpha]_D^{25}$ −9.7°(c=0.2, CH$_3$OH); IR (neat, cm$^{-1}$) 3081 (br),, 3012, 2956, 1747, 1670, 723; $^1$H NMR (CD$_3$COCD$_3$) δ 6.05–5.89 (m, 1H), 5.44–5.14 (m, 10H), 4.72 (dd, J=3.5, 7.7 Hz, 1H), 4.48 (dt, J=1.2, 5.6 Hz, 2H), 2.89–2.69 (m, 6H), 2.38–1.88 (m, 4H), 1.71–1.21 (m, 8H), 0.87 (t, J=6.6 Hz, 3H); MS (FAB) (M+1)$^+$ 401; HRMS calculated for $C_{25}H_{36}O_4$ M$^+$400.2614), found 400.2606; analysis calculated for $C_{25}H_{36}O_4$ +H$_2$O: C,71.74; H, 9.15: Found: C, 71.90; H, 9.11.

(S)-4-Hydroxy-5-[(all-Z)-3,6,9,12-octadecatetraenyl]-3-[(E)-propenyloxy]-2(5H)-furanone.

To a flame-dried, three-necked 250 mL round bottom flask was added, under argon, 0.254 g (0.30 mmol) of [Bis(methyldiphenylphosphine](1,5-cyclooctadiene)iridium(I) hexafluorophosphate suspended in 50 mL of freshly distilled peroxide free anhydrous tetrahydrofuran. The flask was evacuated, and the argon displaced with hydrogen. The red colored suspension turned to a colorless solution and afeer 5 minutes the flask was evacuated and replaced with argon. The (S)-3-(allyloxy)-4-hydroxy-5-[(all-Z)-3,6,9,12-octadecatetraenyl]-2(5H)-furanone (0.6 g, 1.5 mmol), dissolved in 25 mL of peroxide free tetrahydrofuran, was added and reaction completion monitored using TLC (approximately 3 hours). The solvent was evaporated under reduced pressure and the residue was purified over silica gel using 10% methanol in chloroform as eluant to furnish 0.47 g (79%) of dark yellow oil: $[\alpha]_D^{25}$ 11.2° (c=0.2, CH$_3$OH); IR (neat, cm$^{-1}$) 3081(br), 3012, 2956, 1745, 1662, 721; $^1$H NMR (CD$_3$COCD$_3$) δ 6.42–6.35 (m, 1H), 5.49–5.23 (m, 8H), 5.05–4.89 (m, 1H), 4.77 (dd, J=3.5, 7.9 Hz, 1H), 2.92–2.74 (m, 4H), 2.31–1.57 (m, 6H), 1.51 (dd, J=1.6, 6.9 Hz, 3H), 1.45–1.28 (m, 8H), 0.87 (t, J=6.4 Hz, 3H); MS(FAB) (M+1)$^+$ 401, (M+Na)+423; HRMS calculated for $C_{25}H_{36}O_4$ (M$^+$) 400.2614, found 400.2616; analysis calculated for $C_{25}H_{36}O_4$+H$_2$O: C, 71.74; H, 9.15: Found: C, 71.70; H, 9.06.

(S)-3,4-Dihydroxy-5-[(all-Z)-3,6, 9,12-octadecatetraenyl]-2 (5H)-furanone.

To a 100 mL round bottom flask was added, under nitrogen, 0.3 g (0.74 mmol) of (S)-4-hydroxy-5 [(all-Z)-3,6,9,12-octadecatetraenyl]-3-[(E-propenyloxy]-2(5H)-furanone dissolved in 60 mL of 50% aqueous acetic acid. The stirred solution was heated a reflux (oil bath) for 15 minutes, cooled, and concentrated in vacuo. The residue was chromatographed on silica gel using 12% methanol in chloroform as eluant to provide 0.26 g (95%) of yellow oil: $[\alpha]_D^{25}$ −13.5° (c=0.2, CH$_3$OH); IR (neat, cm$^{-1}$) 3220 (br), 3012, 2956, 1751, 1670, 1652, 723, 694; $^1$H NMR (CD$_3$COCD$_3$) δ 5.48–5.34 (m, 8H), 4.68 (dd, J=3.4, 7.9 Hz, 1H), 2.85–2.72 (m, 4H), 2.25–2.19 (m, 2H), 2.18–1.97 (m, 4H), 1.65–1.52 (m, 1H), 1.48–1.28 (m, 7H), 0.87 (t, J=6.7 Hz, 3H); HRMS calculated for $C_{22}H_{32}O_4$ (M$^+$) 360.2301, found 360.2308; analysis calculated for $C_{22}H_{32}O_4$+0.33 H$_2$O: C, 72.1; H, 8.98: Found: C, 72.18; H, 8.93.

EXAMPLE 2

Methyl (R)-2-(2-Allyloxy)acetyloxyarachidonate was prepared as for the S-isomer from methyl (R)-2-hydroxyarachidonate in similar yield: $[\alpha]_D^{25}$ 7.5° (c=0.1, CH$_3$OH); IR (neat, cm$^{-1}$) 3012, 2956, 1756, 1648; $^1$H NMR (CDCl$_3$) δ 5 5.94–5.82 (m, 2H), 5.45–5.22 (m, 10H), 5.11 (t, J=6.3 Hz, 1H); 4.23 (d, J=16.6 Hz, 1H), 4.22 (d, J=6.6, 1H), 4.12 (dt, J=1.3, 5.7 Hz, 2H), 3.75 (s, 3H), 2.89–2.68 (m, 4H), 2.28–1.89 (m, 6H), 1.61–1.49 (m, 2H), 1.42–1.31 (m, 6H), 0.89 (t, J=6.5 Hz, 3H); HRMS calculated for $C_{26}H_{40}O_5$ (M$^+$), 432.2875, found 432.2858.

(R)-3-(Allyloxy)-4-hydroxy-5-[(all-Z)-3,6,9,12-octadecatetraenyl]-2 (5H)-furanone was prepared as for the S-isomer from methyl (R)-2 -hydroxyarachidonate, (allyloxy)acetate in similar yield: $[\alpha]_D^{25}$ 9.4° (c=0.3, CH$_3$OH); IR (neat, cm$^{-1}$) 3081(br), 3012, 2956, 174,9, 1670, 723; $^1$H NMR (CD$_3$COCD$_3$) δ 6.05–5.89 (m, 1H), 5.44–5.14 (m, 10H), 4.74 (dd, J=3.5, 7.7 Hz, 1H), 4.48 (dt, J=1.1, 5.7 Hz, 2H), 2.87–2.69 (m, 6H), 2.42–1.88 (m, 4H), 1.71–1.21 (m, 8H), 0.87 (t, J=6.6 Hz, 3H); MS (FAB) (M+1)$^+$401; HRMS calculated for $C_{25}H_{36}O_4$ (M$^+$) 400.2614, found 400.2607.

(R)-4 -Hydroxy-5-[(all -Z)-3,6,9,12 -octadecatetraenyl]-3-[(E)-propenyloxy]-2(5H)-furanone was prepared as for the S-isomer from (R)-3-(Allyloxy)-4-hydroxy-5-[(all-Z)-3, 6,9,12-octadecatetraenyl]-2(5H)-furanone in similar yield $[\alpha]_D^{25}$ 11.7° (c=0.2 CH$_3$OH); IR (neat cm$^{-1}$) 3081(br), 3012, 2956, 1749, 1664, 696; $^1$H NMR (CD$_3$COCD$_3$) δ6.42–6.35 (m, 1H), 5.49–5.23 (m, 8H), 5.05–4.89 (m, 1H) 4.77 (dd, J=3.5, 7.9 Hz, 1H), 2.92–2.74 (m, 4H), 2.31–1.57 (m, 6H), 1.51 (dd, J=1.6, 6.9 Hz, 3H), 1.45–1.28 (m, 8H), 0.87 (t, J=6.4 Hz, 3H); MS(FAB) (M+1)$^+$ 401, (M+Na)$^+$423; HRMS calculated for $C_{25}H_{36}O_4$ (M$^+$) 409.2614, found 400.2615.

(R)-3,4-Dihydroxy-5-[all-Z)-3,6,9,12-octadecatetraenyl]-2(51H)-furanone was prepared as for the S-isomer from (R)-4-Hydroxy-5-[(all-Z)-3,6,9,12-octadecatetraenyl]-3-[(E)-propenyloxy]-2(5H)-furanone in similar yield: $[\alpha]_D^{25}$ 13.2°(c=0.2, CH$_3$OH); IR (neat, cm$^{-1}$) 3241 (br), 3012, 2956, 1751, 1675, 1652, 723, 694; $^1$H NMR (CD$_3$COCD$_3$) δ 5.48–5.34 (m, 8H), 4.68 (dd, J=3.4, 7.9 Hz, 1H), 2.85–2.72 (m, 4H), 2.35–2.19 (m, 2H), 2.18–1.97 (m, 4H), 1.65–1.52 (m, 1H), 1.48–1.28 (m, 7H), 0.87 (t, J=6.7 Hz, 3E); HRMS calculated for $C_{22}H_{32}O_4$ (M$^+$) 360.2301, found 360.2305; analysis calculated for $C_{22}H_{32}O_4$ +0.5 H$_2$O: C, 71.51; H, 9.00; Found: C, 71.52; H, 9.14.

EXAMPLE 3

Methyl (2S, 5Z)-2-(2-Allyloxy) acetyloxy-5-eicosenoate.

To a dry 100 mL three-necked round bottom flask fitted with a rubber septum was added, under argon, 0.65 g (1.91 mmol) of methyl (2S,5Z)-2-hydroxy-5-eicosenoate and 50 mL of anhydrous $CH_2Cl_2$. Following cooling to 10° C. (ice bath), 0.45 g (3.82 mmol) of allyloxyacetic acid dissolved in 15 mL of anhydrous $CH_2Cl_2$ and 0.028 g (0.19 mmol) of 4-pyrrolidinopyridine dissolved in 2 mL of anhydrous $CH_2Cl_2$ were added. A solution containing 0.79 g (3.82 retool) of DCC in 15 mL of $CH_2Cl_2$ was added dropwise and the stirred mixture was warmed to room temperature and stirred for an additional 8 hours. $CH_2Cl_2$ was evaporated in vacuo and the product was purified over silica gel using ethyl acetate:hexanes (1:5) as eluant to furnish 0.78 g (93%) of colorless oil: $[\alpha]_D^{25}$ −6.5° (c=1.6, $CH_3OE$); IR (neat, $cm^{-1}$) 3006, 2923, 1758, 721; $^1H$ NMR ($CD_3COCD_3$) δ 6.01–5.86 (m, 1H), 5.51–5.24 (m, 4H), 5.10 (t, J=6.3 Hz, 1H), 4.22 (d, J=16.6 Hz, 1H), 4.23 (d, J=16.6 Hz, 1H), 4.13 (dr, J=1.1, 5.7 Hz, 2H), 3.75 (s, 3H), 2.26–2.12 (m, 2H), 2.07–1.87 (m, 4H), 1.42–1.28 (m, 24H), 0.88 (t, J=6.3 Hz, 3H); HRMS calculated for $C_{26}H_{46}O_5$ ($M^+$), 438.3345 found 438.3330.

(S)-3-Allyloxy-4-hydroxy-5-[(Z)-3-octadecenyl]-2(5H)-furanone.

To a flame-dried, three-necked 250 mL round bottom flask fitted with a low temperature thermometer and a septum was added, under argon, 0.648 g (4.02 mmol) of hexamethyldisilazane in 50 mL of anhydrous tetrahydrofuran. The contents were cooled to −25° C. (dry-ice/$CCl_4$), and 2.51 mL of 1.6M (4.02 mmol) of n-BuLi in hexanes was added dropwise with stirring while maintaining the temperature below −15° C. The mixture was warmed to −5° C. and the contents maintained between −5° C. and 0° C. for 45 minutes. The mixture was cooled to −78° C. (dry ice/acetone) and 0.84 g (1.91 mmol) methyl (2S, 5Z)-2-(2-allyloxy)acetyloxy-5-eicosenoate in 20 mL of anhydrous tetrahydrofuran was added dropwise with stirring while maintaining the temperature below −68° C. Following addition, the mixture was stirred at −78° C. for 75 minutes and quenched with 10 mL of 10% aqueous Hcl solution. Ether (75 mL) was added, and the reaction mixture was warmed to room temperature and extracted with 3×75 mL of ether. The ether extracts were washed with 2×50 mL of brine, dried ($Na_2SO_4$) and concentrated in vacuo to provide 0.75 g (97%) of residue. Purification over silica gel using 10% methanol in chloroform as eluant provided 0.69 g (89%) of white solid: mp 51°–54° C.; $[\alpha]_D^{25}$ 9.0° (c=0.6, $CH_3OH$); IR (neat, $cm^{-1}$) 3079 (br), 3002, 2915, 1741, 1654, 734, 719; $^1H$ NMR ($CD_3COCD_3$) δ6.04–5.89 (m, 1H), 5.47–5.15 (m, 4H), 4.72 (dd, J=3.5, 7.6 Hz, 1H), 4.48 (dr, J=1.1, 5.9 Hz, 2H), 2.21–1.54 (m, 6H), 1.45–1.28 (m, 24H), 0.87 (t, J=6.8 Hz, 3H); HRMS calculated for $C_{25}H_{42}O_4$ ($M^+$) 406. 3083, found 406. 3084; analysis calculated for $C_{25}H_{42}O_4$: C, 73.85; H, 10.41. Found: C, 73.52; H, 10.27.

(S)-4-Hydroxy-5-[(Z)-3-octadecenyl]-3-[(E)-propenyloxy]-2(5H)-furanone.

To a flame-dried, three-necked 250 mL round bottom flask under argon was added 0.172 g (0.20 mmol) of [bis(methyldiphenylphosphine)](1,5-cyclooctadiene) iridium(1) hexafluorophosphate suspended in 35 mL of freshly distilled peroxide free anhydrous tetrahydrofuran. The flask as evacuated and the argon displaced with hydrogen. The red suspension turned to a colorless solution after 5 minutes. The flask was evacuated, and the hydrogen replaced with argon. (S)-3-allyloxy-4-hydroxy-5-[(Z)-3-octadecenyl]-2(5H)-furanone (0.415 g, 1.02 mmol) was dissolved in 25 mL of peroxide free tetrahydrofuran and added to the activated catalyst. On completion (TLC; approximately 3 hours) the solvent was evaporated in vacuo and purified over silica gel using 10% methanol in chloroform as eluant to provide 0.33g (79%) of white waxy solid: mp 42°–45° C.; $[\alpha]_D^{25}$ −13.0°(c=0.3, $CH_3OH$); IR (neat, $cm^{-1}$) 3079 (br), 3004, 2919, 1739, 1681, 1658, 738, 721; $^1H$ NMR ($CD_3COCD_3$ δ 6.43–6.36 (m, 1H), 5.49–5.31 (m, 2H), 5.05–4.91 (m, 1H), 4.77 (dd, J=3.5, 7.8 Hz, 1H), 2.24–1.62 (m, 6H), 1.51 (dd, J=1.7, 6.9 Hz, 3H), 1.44–1.24 (m, 24H), 0.87 (t, J=6.8 Hz, 3H); HRMS calculated for $C_{25}H_{42}O_4$ ($M^+$) 406.3083, found 406.3083.

(S)-3,4-Dihydroxy-5-[(Z)-3-octadecenyl]-2(5H)-furanone.

To a 100 mL round bottom flask was added, under nitrogen, 0.2 g (0.49 mmol) (S)-4-hydroxy-5-[(Z)-3-octadecenyl]-3-[(E)-propenyloxy]-2(5H)-furanone was dissolved in 60 mL of 50% aqueous acetic acid. The solution was heated at reflux (oil bath) for 15 minutes, cooled, and the aqueous acetic acid removed in vacuo. The residue was purified over silica gel using 12% methanol in chloroform as eluant to give 0.17 g (95%) of white waxy solid: mp 64°–66°C; $[\alpha]_D^{25}$ −9.9° (C=0.5, $CH_3OH$); IR (neat, $cm^{-1}$) 3421(br), 2917, 2850, 1754, 1668, 719; $^1H$ NMR ($D_3COCD_3$) δ5.49–5.28 (m, 2H), 4.67 (dd, J=3.4, 7.8 Hz, 1H), 2.32–1.88 (m, 4H), 1.69–1.51 (m, 2H), 1.44–1.25 (m,. 24H), 0.87 (t, J=6.7 Hz, 3H); HRMS calculated for $C_{25}H_{38}O_4$ ($M^+$) 366.2770, found 366.2780; analysis calculated for $C_{22}H_{38}O_4$+0.33 $H_2O$: C, 70.93; H, 10.46; Found: C, 70.73; H, 10.31.

EXAMPLE 4

Methyl (2R, 5Z)-2-(2-Allyloxy)acetyloxy-5-eicosenoate was prepared as for the S-isomer from methyl (2R, 5Z)-2-hydroxy-5-eicosenoate (as prepared as Example D) in similar yield: $[\alpha]_D^{25}$ 6.4° (c=1.4, $CH_3OH$); IR (neat, $cm^{-1}$) 3006, 2921, 1756, 721; $^1H$ NMR ($CD_3COCD_3$) δ 6.01–5.86 (m, 1H), 5.51–5.24 (m, 4H), 5.10 (t, J=6.3 Hz, 1H), 4.22 (d, J=16.6 Hz, 1H), 4.23 (d, J=16.6 Hz, 1H), 4.13 (dt, J=1.1, 5.7 Hz, 2H), 3.75 (s, 3H), 2.26–2.12 (m, 2H), 2.07–1.87 (m, 4H), 1.42–1.28 (m, 24H), 0.88 (t, J=6.3 Hz, 3H); HRMS calculated for $C_{25}H_{46}O_5$ ($M^+$) 438.3345, found 438. 3347.

(R)-3-Allyloxy-4-hydroxy-5-[(Z)-3-octadecenyl]-2(5H)-furanone was prepared as for the S-isomer from methyl (2R, 5Z)-2-(2-allyloxy) acetyloxy-5-eicosenoate in similar yield: mp 49°–53° C.; $[\alpha]_D^{25}$ 8.9° (c=0.8, $CH_3OH$); IR (neat, $cm^{-1}$) 3079 (br), 3002, 2915, 1741, 1654, 734, 719; $^1H$ NMR ($CD_3COCD_3$) δ 6.04–5.89 (m, 1H), 5.47–5.15 (m, 4H), 4.72 (dd, J=3.5, 7.6 Hz, 1H), 4.48 (dt, J=1.1, 5.9 Hz, 2H), 2.21–1.54 (m, 6H), 1.45–1.28 (m, 24H), 0.87 (t, J=6.8 Hz, 3H); HRMS calculated for $C_{25}H_{42}O_4$ ($M^+$), 406.3083 found 406.3094.

(R)-4-Hydroxy-5-[(Z)-3-octadecenyl]-3-[(E)-propenyloxy]-2(5H)-furanone was prepared as for the S-isomer from (R)-3-Allyloxy-4-hydroxy-5-[(Z)-3-octadecenyl]-2(5H)-furanone in similar yield: mp 42°–45° C.; $[\alpha]_D^{25}$ 12.8° (c=0.3, $CH_3OH$); IR (neat, $cm^{-1}$) 3079 (br), 3004, 2919, 1739, 1681, 1658, 738, 721; $^1H$ NMR ($CD_3COCD_3$) δ 6.43–6.36 (m, 1H), 5.49–5.31 (m, 2H), 5.05–4.91 (m, 1H), 4.77 (dd., J=3.5, 7.8 Hz, 1H), 2.24–1.62 (m, 6H), 1.51 (dd, J=1.7, 6.9 Hz, 3H), 1.44–1.24 (m, 24H), 0.87 (t, J=6.8 Hz, 3H); HRMS calculated for $C_{25}H_{42}O_4$ ($M^+$) 406.3083, found 406, 3076.

(R)-3,4-Dihydroxy-5-[(Z)-3-octadecenyl]-2(5H)-furanone was prepared as for the S-isomer from (R)-4-hydroxy-5-[(Z)-3-octadecenyl]-3-[(E)-propenyloxy]-2(5H)-furanone in similar yield: mp 65°–67° C.; $[\alpha]_D^{25}$ 9.5° (c=0.5 $CH_3OH$); IR (neat, $cm^{-1}$) 3421 (br), 2917, 2850, 1754, 1666, 734, 719; $^1H$ NMR ($CD_3COCD_3$) δ 5.49–5.28 (m, 2H), 4.67 (dd, J=3.4, 7.8 Hz, 1H), 2.32–1.88 (m, 4H), 1.69–1.51 (m, 2H), 1.44–1.25 (m, 24H), 0.87 (t, J=6.7 Hz, 3H); HRMS calculated for $C_{22}H_{38}O_4$ ($M^+$), 366.2770 found 366.2780; analysis calculated for $C_{22}H_{38}O_4+0.33\ H_2O$: C, 70.93; H, 10.46: Found: C, 70.53; H, 10.25.

EXAMPLE 5

Methyl (2S, 5Z)-2-(2-Benzyloxy) acetyloxy-5-eicosenoate.

To a two-necked, flame-dried 100 mL round bottom flask was added, under argon, 0.275 g (0.81 mmol) of methyl (2S,5Z)-2-hydroxy-5-eicosenoate in 40 mL of anhydrous $CH_2Cl_2$ and 0.20 g (1.09 mmol) of benzyoxyacetyl chloride. The solution was cooled to 0° C. (ice-salt bath), and pyridine (0.086 g, 1.09 mmol) was added dropwise. The mixture was stirred for 30 minutes at 0° C., warmed to room temperature, and stirred for an additional 8 hours. The reaction was quenched with 10 mL of ice-water. $CH_2Cl_2$ (20 mL) was added, and the mixture stirred for 6 hours. The $CH_2Cl_2$ layer was washed with 3×20 mL 10% aqueous Hcl solution, 3×15 mL of saturated sodium bicarbonate solution, 2×25 mL of brine, dried ($Na_2SO_4$) and concentrated under reduced pressure. The residue was purified over silica gel using ethyl acetate:hexanes (1:5) as eluant to yield 0.34 g (87%) of white solid: $[\alpha]_D^{25}$ -5.4° (c=0.5, $CH_3OH$); IR (neat, $cm^{-1}$) 3006 (br), 2923, 1756, 1455, 734, 698; $^1H$ NMR ($CD_3COCD_3$) δ 7.40-7.26 (m, 5H), 5.48-5.22 (m, 2H), 5.12 (t, J=16.7 Hz, 1H); 4.17 (d, J=16.7 Hz, 1H), 3.76 (s, 3H); 2.20-1.87 (m, 6H), 1.49-1.21 (m, 24H), 0.88 (t, J=6.4 Hz, 3H); HRMS calculated for $C_{30}H_{48}O_5$ ($M^+$), 488.3501, found 488.3501.

(S)-3-Benzyloxy-4-hydroxy-5-[(Z)-3-octadecenyl]-2(5H)-furanone.

To a flame-dried, three-necked 100 mL flask equipped with a low temperature thermometer was added, under argon, 0.302 g (1.87 mmol) of hexamethyldisilazide in 25 mL of anhydrous tetrahydrofuran. The solution was cooled to -25° C. and 1.17 mL of 1.6 M n-BuLi (1.87 mmol) in hexanes was added dropwise with stirring while maintaining the temperature below -15° C. The reaction was held between -3° C. and -5° C. for 45 minutes, cooled to -78° C., and 0.434 g (0.89 retool) of methyl (2S,5Z)-2-hydroxy-5-eicosenoate, (benzyloxy)acetate in 8 mL of anhydrous tetrahydrofuran was added dropwise. The reaction was stirred for 2 hours and quenched at -78° C. with 10 mL of cooled 10% aqueous Hcl solution. Ether (15 mL) was added, and the mixture was warmed to room temperature and extracted with 3×50 mL of ether. The organic layers were washed with 3×25 mL of brine, dried ($Na_2SO_4$) and concentrated under reduced pressure. The residue was purified over silica gel using 10% methanol in chloroform as eluant to furnish 0.34 g (84%) of white solid: mp 76°-79° C.; $[\alpha]_D^{25}$ -13.8° (c=0.3, $CH_3OH$); IR (KBr, $cm^{-1}$) 3033 (br), 3004, 2917, 1739, 1660, 1402, 1342, 738, 728, 696; $^1H$ NMR ($CD_3COCD_3$) δ 7.43-7.29 (m, 5H), 5.48-5.27 (m, 2H), 5.06 (d, J=11.3 Hz, 1H), 5.01 (d, J=11.3 Hz, 1H); 4.69 (dd, J=3.5, 7.6 Hz, 1H), 2.28-1.51 (m, 6H), 1.42-1.27 (m, 24H), 0.86 (t, J=6.7 Hz, 3H); HRMS calculated for $C_{29}H_{44}O_4$ ($M^+$), 456.3239; analysis calculated for $C_{29}H_{44}O_4+0.2\ H_2O$: C, 75.68; H, 9.72; Found: C, 75.57; H, 9.68.

(S)-3,4-Dihydroxy-5-octadecyl-2(5H)-furanone.

To a 250 mL hydrogenation bottle was added 0.02 g of 10% palladium on carbon in 5 mL methanol. To this suspension was added 0.1 g (0.219 mmol) of (S)-3-benzyloxy-4-hydroxy-5-[(Z)-3-octadecenyl]-2(5H)-furanone dissolved in 15 mL methanol. Hydrogenation was initiated at 40 psi and at room temperature. The reaction was monitored for completion by TLC (approximately 5-6 hours), filtered (Celite) and evaporated under reduced pressure. The residue was purified over silica gel using 10% methanol in chloroform as eluant to generate 58 mg (72%) of white solid: mp 110°-112° C.; $[\alpha]_D^{25}$ -6.8° (c=0.3, $CH_3OH$); IR (Kbr, $cm^{-1}$) 3380 (br), 2917, 2848, 1741, 1668; $^1H$ NMR ($CD_3COCD_3$) δ 4.67 (dd, J=3.5, 7.3 Hz, 1H), 2.01-1.88 (m, 1H), 1.57-1.47 (m, 1H), 1.42-1.23 (m, 322), 0.87 (t, J=6.8 Hz, 3H); HRMS calculated for $C_{22}H_{40}O_4$ ($M^+$), 368.2927, found 368.2928; analysis calculated for $C_{22}H_{40}O_4+0.5\ H_2O$: C, 69.99; H, 10.95; Found: C, 70.27; H, 11.22.

EXAMPLE 6

Methyl (2R, 5Z)-2-(2-Benzyloxy) acetyloxy-5-eicosenoate was prepared as for the S-isomer from methyl (2R,5Z)-2-hydroxy-5-eicosenoate in similar yield: $[\alpha]_D^{25}$ 5.2° (c=0.5, $CH_3OH$); IR (neat, $cm^{-1}$) 3006, 2923, 1756, 1455, 734, 698; $^1H$ NMR ($CD_3COCD_3$) δ 7.40-7.26 (m, 5H), 5.48-5.22 (m, 2H), 5.12 (t, J=6.4 Hz, 1H); 4.66 (s, 2H), 4.25 (d, J=16.7 Hz, 1H); 4.17 (d, J=1617 Hz, 1H), 3.76 (s, 3H), 2.20-1.87 (m, 6H), 1.49-1.21 (m, 24H), 0.88 (t, J=6.4 Hz, 3H); HRMS calculated for $C_{30}H_{48}O_5$ ($M^+$), 488.3501, found 488.3501.

(R)-3-Benzyloxy-4-hydroxy-5-[(Z)-3-octadecenyl]-2(5H)-furanone was prepared as for the S-isomer from methyl (2R, 5Z)-2-(2-benzyloxy) acetyloxy-5-eicosenoate in similar yield: mp 76°-79° C. $[\alpha]_D^{25}$ 13.5° (c=0.5, $CH_3OH$); IR (Kbr, $cm^{-1}$) 3033 (br), 3004, 2917, 1739, 1660, 1400, 1342, 738, 730; 696; $^1H$ NMR ($CD_3COCD_3$) δ 7.43-7.29 (m, 5H), 5.48-5.27 (m, 2H), 5.06 (d, J=11.3 Hz, 1H); 5.01 (d, J=11.3 Hz, 1H); 4.67 (dd, J=3.5, 7.6 Hz, 1H), 2.28-1.51 (m, 6H), 1.42-1.27 (m, 24H), 0.86 (t, J=6.7 Hz, 3H); HRMS calculated for $C_{29}H_{44}O_4$ ($M^+$), 456.3239, found 456.3243.

(R)-3,4-Dihydroxy-5-[3-octadecyl]-2(5H)-furanone was prepared as for the S-isomer from (R)-3-benzyloxy-4-hydroxy-5-[Z)-3-octadecenyl]-2(5H)-furanone in similar yield: mp 114°-117° C.; $[\alpha]_D^{25}$ 5.2° (c=0.2, $CH_3OH$); IR (Kbr, $cm^{-1}$) 3411 (br), 2917, 2848, 1754, 1668; $^1H$ NMR ($CD_3COCD_3$) δ 4.67 (dd, J=3.5, 7.3 Hz, 1H), 2.01-1.88 (m, 1H), 1.57-1.47 (m, 1H), 1.42-1.23 (m, 32H), 0.87 (t, J=6.8 Hz, 3H); HRMS calculated for $C_{22}H_{40}O_4$ ($M^+$), 368.2927, found 368.2927; analysis calculated for $C_{22}H_{40}O_4+0.5\ H_2O$: C, 69.99; H, 10.95; Found C: 69.71; H, 11.09.

EXAMPLE 7

Methyl (S)-3-phenyllactate.

In a 250 mL round bottom flask fitted with a reflux condenser, 3.0 g (18.07 mmol) of S-phenyllactic acid in 225 mL of methanol containing 4 drops of concentrated sulfuric acid was heated at reflux for 7 hours. The reaction mixture was cooled, 0.6 g of sodium bicarbonate was added, and the methanol was evaporated under reduced pressure. The residue was taken up in 200 mL of ether, and the ether layer was washed with 2×75 mL of water, 2×100 mL of saturated sodium bicarbonate solution and 2×75 mL of brine, dried ($Na_2SO_4$) and evaporated under reduced pressure to provide 3.12 g of crude product which was purified over silica gel using ethyl acetate:hexanes (1:5) to furnish 2.92 g (90%) of white crystalline solid: mp 46°-47° C., IR (Kbr, $cm^{-1}$) 3473 (br), 3029, 2954, 1739, 1496, 1454; $^1H$ NMR ($CDCl_3$) δ 7.34-7.19 (m, 5H), 4.50-4.43 (m, 1H), 3.77 (s, 3H), 3.14 (dd, J=4.4, 13.9 Hz, 1H); 2.96 (dd, J=6.8, 13.9 Hz, 1H), 2.72 (d, J=6.2 Hz, 1H); HRMS calculated for $C_{10}H_{12}O_3$ ($M^+$), 180.0786, found 180.0786.

Methyl (S)-2-(2-Benzyloxy)acetyloxy-3-phenyllactate.

To a two-necked, flame-dried 250 mL round bottom flask, under argon, was added 2.92 g (16.2 mmol) of methyl (S)-3-phenyllactate in 80 mL of anhydrous $CH_2Cl_2$. Benzyloxyacetyl chloride (4.49 g, 24.33 mmol) was added with stirring and the solution was cooled to 0° C. in an ice-salt bath. Pyridine (1.93 g, 24.33 mmol) was added dropwise and reaction contents were stirred for 30 minutes at 0° C., warmed to room temperature, and stirred for an additional 3 hours. The reaction was quenched with 40 mL of ice-water and 75 mL of $CH_2Cl_2$ was added. Following stirring overnight the $CH_2Cl_2$ layer was washed with 3×75 mL of 10% aqueous HCl solution, 3×100 mL of saturated sodium bicarbonate under reduced pressure. The crude product was purified over silica gel using ethyl acetate:hexanes (1:5) to yield 4.68 g (88%) of white crystalline solid: mp 51°–52° C., $[\alpha]_D^{25}$ –14.3° (c=2.4, $CH_3OH$); IR (Kbr, $cm^{-1}$) 2948, 2886, 1766, 1745, 1455, 1434; $^1H$ NMR ($CDCl_3$) δ 7.36–7.19 (m, 10H), 5.36 (dd, J,=4.5, 8.7 Hz, 1H); 4.57 (s, 2H), 4.19 (d, J=16.7 Hz, 1H); 4.09 (d, J=16.7 Hz, 1H), 3.74 (s, 3H), 3.23 (dd, J=4.5, 14.3 Hz, 1H), 3.11 (dd, J=8.7, 14.3 Hz, 1H); HRMS calculated for $C_{19}H_{20}O_5$ ($M^+$), 328.1311, found 328.1269.

(S)-5-Benzyl-3-benzyloxy-4-hydroxy-2(5H)-furanone.

To a flame-dried three-necked argon-purged 100 mL flask equipped with a low temperature thermometer was added 2.38 g (14.73 mmol) of hexamethyldisilazide in 35 mL of anhydrous tetrahydrofuran. The solution was cooled to –25° C., and 5.9 mL of a 2.5 M n-BuLi (14.73 mmol) solution in hexanes was added dropwise while maintaining the temperature below –15° C. Following the addition, the reaction was stirred and held between –3 and –5° C. for 45 minutes and cooled to –78° C. Methyl (S)-2-(2-benzyloxy) acetyloxy-3-phenyllactate (2.3 .g, 7.01 mmol) in 10 mL of anhydrous tetrahydrofuran was added dropwise. The reaction was stirred for 75 minutes and quenched at –78° C. with 25 mL of precooled 10% aqueous HCl solution. After warming to room temperature, the aqueous layer was extracted with 3×80 mL of ether and the combined organic layers washed with 3×100 mL of brine and dried ($Na_2SO_4$). The ether was evaporated under reduced pressure to provide 1.98 g of crude white solid which was recrystallized using ether/petroleum ether to give 1.82 g (85%) of white crystalline solid: mp 181°–182° C.; $[\alpha]_D^{25}$ –57.1°(c=0.9, $CH_3OH$); IR (Kbr, $cm^{-1}$) 3031 (br), 2719., 1743, 1662, 1454; $^1H$ NMR ($CD_3COCD_3$) δ 7.34–7.29 (m, 5H), 7.29–7.21 (m, 5H), 4.96 (dd, J=3.7, 6.5 Hz, 1H), 4.87 (d, 18.2 Hz, 1H), 4.79 (d, J=18.2 Hz, 1H), 3.26 (dd, J=3.7, 14.5 Hz, 1H), 2.88 (dd, J=6.5, 14.5 Hz, 1H); $^{13}C$ NMR ($CD_3COCD_3$) δ 169.0, 160.2, 138.2, 136.4, 130.6 (2C), 129.2 (2C), 129.1 (2C), 129.0 (2C), 128.8, 127.6, 121.9, 76.0, 73.6, 38.6; HRMS calculated for $C_{18}H_{16}O_4$ ($M^+$), 296. 1048, found 296.1045; analysis calculated for $C_{18}H_{16}O_4$: C, 72.96; H, 5.44; Found C: 72.59; H, 5.53.

(S)-5-Benzyl-3,4-dihydroxy-2(5)H-furanone.

In a 250 mL argon-flushed hydrogenation bottle was suspended 0.2 g of palladium on 10% carbon in 10 mL methanol. To this suspension was added 2.0 g (6.76 retool) of (S)-5-benzyl-3-benzyloxy-4-hydroxy-2 (5H)-furanone and 25 mL methanol. The mixture was shaken at room temperature under hydrogen (35 psi) and monitored by TLC (about 5–6 hours). After filtration (Celite pad) the filtrate was evaporated under reduced pressure, and the residue was purified by recrystallization from acetone/hexanes to furnish 1.25 g (90%) of a white crystalline solid: mp 142°–144° C.; $[\alpha]_D^{25}$ –40.2°(c=2.1, $CH_3OH$); IR (Kbr, $cm^{-1}$) 3334 (br), 1762, 1681, 1455, 1319; $^1H$ NMR ($CD_3COCD_3$) δ 7.28–7.21 (m, 5H), 4.93 (dd, J=3.5, 6.7 Hz, 1H), 3.29 (dd, J=3.5, 14.5 Hz, 1H), 2.88 (dd, J=6.5, 14.5 Hz, 1H);. HRMS calculated for $C_{11}H_{10}O_4$ ($M^+$), 206.0579, found 206.0583; analysis calculated for $C_{11}H_{10}O_4$: C, 64.08; H, 4.82; Found C: 63.99; H, 4.89.

EXAMPLE 8

Methyl (R)-3-phenyllactate was prepared in similar yield as for the corresponding S-isomer from (R)-phenyllactic acid: mp 47° C.; IR (Kbr, $cm^{-1}$) 3479 (br), 3029, 2954, 1739, 1496, 1454; $^1H$ NMR ($CDCl_3$ δ 7.34–7.19 (m, 5H), 4.50–4.43 (m, 1H), 3.78 (s, 3H), 3.14 (dd, J=4.3, 13.9 Hz, 1H), 2.97 (dd, J=6.8, 13.9 Hz, 1H), 2.72 (d, J=6.2 Hz, 1H); HRMS calculated for $C_{10}H_{12}O_3$ ($M^+$), 180.0786, found 180.0795.

Methyl (R)-2-(2-Benzyloxy) acetyloxy-3-phenyllactate was prepared in similar yield as for the corresponding S-isomer from (R)-3-phenyllactate: mp 49°–50° C.; $[\alpha]_D^{25}$ 14.7°(c=0.4, $CH_3OH$); IR (Kbr, $cm^{-1}$) 2948, 2886, 1766, 1745, 1455, 1434. $^1H$ NMR ($CDCl_3$) δ 7.35–7.19 (m, 10H), 5.36 (dd, J=4.5, 8.7 Hz, 1H), 4.57 (s, 2H), 4.19 (d, J=16.7 Hz, 1H), 4.09 (d, J=16.7 Hz, 1H), 3.74 (s, 3H), 3.23 (dd, J=4.5, 14.3 Hz, 1H), 3.11 (dd, J=8.7, 14.3 Hz, 1H); HRMS calculated for $C_{19}H_{20}O_5$ ($M^+$), 328.1311, found 328.1303.

(R)-5-Benzyl-3-benzyloxy-4-hydroxy-2(5H)-furanone was prepared in similar yield as for (S)-5-benzyl-3-benzyloxy-4-hydroxy-2 (5)H -furanone from methyl (R)-2-(2-benzyloxy) acetyloxy-3-phenyllactate: mp 182°–183° C.; $[\alpha]_D^{25}$ 57.8° (c=0.4, $CH_3OH$); IR (Kbr, $cm^{-1}$) 3029 (br), 2717, 1743, 1660, 1454, $^1H$ NMR ($CD_3COCD_3$) δ 7.34–7.29 (m, 5H), 7.29–7.21 (m, 5H), 4.96 (dd, J=3.7, 6.5 Hz, 1H), 4.86 (d, 18.4 Hz, 1H), 4.79 (d, J=18.4 Hz, 1H), 3.26 (dd, J=2.7, 14.4 Hz, 1H), 2.88 (dd, J=6.5, 14.4 Hz, 1H); HRMS calculated for $C_{18}H_{16}O_4$ ($M^+$), 296.1048, found 296.1045.

(R)-5-Benzyl-3,4-dihydroxy-2(5H)-furanone was prepared in similar yield as for the corresponding S-isomer from (R)-5-benzyl -3-benzyloxy-4-hydroxy-2(5H)-furanone : mp 142°–144° C.; $[\alpha]_D^{25}$ 40.8° (c=0.8, $CH_3$); IR (Kbr, $cm^{-1}$) 3336 (br), 1762, 1679, 1455, 1319; $^1H$ NMR ($CD_3COCD_3$) δ 7.28–7.22 (m, 5), 4.93 (dd, J=3.6, 6.7 Hz, 1H), 3.29 (dd, J=3.6, 14.5 Hz, 1H), 2.88 (dd, J=6.7, 14.5 Hz, 1H); HRMS calculated for $C_{11}H_{10}O_4$: C, 64.08; H, 4.82. Found: C, 63.93, H, 4.86.

EXAMPLE 9

(S)-5-(2-Hydroxyethyl)-2,2-dimethyl-1,3-dioxolan-4-one.

In a 500 mL flame-dried round bottom flask fitted with a septum and under argon was placed 11.0 g (63.2 mmol) of the dioxolanate of (S)-malic acid (prepared by reaction of commercially available (S)-malic acid with excess dimethoxypropane and p-toluenesulfonic acid as a catalyst) dissolved in 200 mL anhydrous tetrahydrofuran. The reaction was cooled (–20° C. to –30° C.) and 70 mL of 1M borane-tetrahydrofuran complex was added dropwise over 2 hours. Following addition the reaction vessel was placed in a refrigerator at 4° C. for 11 hours, warmed to room temperature, stirred at room temperature for 9 hours and chromatographed (silica gel) using acetone as eluant. Following evaporation under reduced pressure, the residue was chromatographed as before to generate 9.1 g (90%) of the alcohol as a colorless unstable liquid which was dried under reduced pressure and utilized as such in the next reaction: IR (neat, $cm^{-1}$) 3480 (br), 2994, 2940, 2888, 1791, 1220; $^1H$ NMR ($CDCl_3$) δ 4.58 (dd, J=5.1, 7.0 Hz, 1H), 3.91–3.79 (m, 2H), 2.28–2.13 (m, 1H), 2.13–1.97 (m, 1H), 1.64 (s, 3H), 1.57 (s, 3H).

(S)-5-(2-Hydroxyethyl)-2,2-dimethyl -1,3-dioxolan-4-one p-toluenesulfonate.

Dried (S)-5-(2-hydroxyethyl)-2,2-dimethyl-1,3-dioxolane-4-one (9.0 g, 59.2 mmol) was dissolved in 100 mL of anhydrous pyridine under argon and cooled to −4° C. To this solution maintained at approximately 0° C. was added dropwise 11.3 g (59.22 mmol) of p-toluenesulfonyl chloride dissolved in 100 mL of pyridine. Following addition, the mixture was placed in the refrigerator (0°–4° C.) overnight. Water (150 mL) was added, and the aqueous mixture extracted with 4×200 mL of ether. The ether layers were combined, washed with 3×150 mL of water, 3×150 mL of saturated copper sulfate solution (until no dark blue color remained), 2×100 mL of water, 3×150 mL of brine, dried ($Na_2SO_4$), filtered, and evaporated under reduced pressure. The crude rosylate was purified by column chromatography using ethyl acetate:hexanes (1:1) to provide the title compound, 16.7 g (95%) as white solid: mp 48°–49° C.; $[\alpha]_D^{25}$ −3.7°(C=0.3, $CH_3OH$); IR (Kbr, $cm^{-1}$) 2989, 1785, 1390, 1357, 1278; $^1H$ NMR ($CDCl_3$) δ 7.80 (d, J=8.3 Hz, 2H), 7.36 (d, J=8.3 Hz, 2H), 4.43 (dd, J=4.4, 8.1 Hz, 1H), 4.27–4.14 (m, 2H), 2.46 (s, 3H), 2.3–2.17 (m, 1H), 2.09–1.92 (m, 1H), 1.58 (s, 3H), 1.51 (s, 3H); HRMS calculated for $C_{14}H_{18}O_6S$ ($M^+$), 314.0824, found 314.0817.

(S)-5-Hexyl-2,2-dimethyl-1,3-dioxolan-4-one.

To a flame-dried 500 mL three-necked round bottom flask under nitrogen containing a suspension of 4.85 g (25.48 mmol) of cuprous iodide in 200 mL of anhydrous ether and held at −30° C. was added dropwise 31.85 mL of 1.6M n-BuLi (50.96 mmol) in hexanes. The dark red-brown solution was stirred at −30° C. to −40° C. for 2 hours and cooled to −78° C. (S)-5-(2-hydroxyethyl)-2,2-dimethyl-1,3-dioxolan-4-one p-toluenesulfonate (4.0 g, 12.74 mmol), dissolved in 30 mL of anhydrous ether and 10 mL of anhydrous tetrahydrofuran, was added dropwise while maintaining the temperature below −70° C. The reaction mixture was stirred for 18 hours at −78° C. Following completion (TLC monitoring), the reaction was warmed to −10° C. and quenched by the addition of 125 mL of precooled saturated ammonium chloride solution. Ether (100 mL) was added and the mixture filtered over Celite. The aqueous phase was extracted with 3×175 mL ether. The combined ether extract was washed with 2×125 mL of saturated ammonium chloride solution, 1×75 mL of water and 2×100 mL of brine, dried ($Na_2SO_4$), filtered and concentrated under reduced pressure. The product was purified (silica gel) using ethyl acetate:hexanes (1:5) as eluant to give 2.44 g (95%) of the title compound as a colorless oil: $[\alpha]_D^{25}$ 0.6°(c=1.9, $CH_3OH$); IR (Kbr, $cm^{-1}$) 2958, 2933, 2861, 1797; $^1H$ NMR ($CDCl_3$) δ 4.39 (dd, J=4.4, 7.1 Hz, 1H), 1.95–1.81 (m, 1H), 1.81–1.62 (m, 1H), 1.61 (s, 3H), 1.54 (s, 3H), 1.49–1.38 (m, 2H), 1.35–1.29 (m, 6H), 0.89 (t, J=6.6 $^{13}C$ NMR ($CDCl_3$) δ 173.3, 110.2, 74.2, 31.7, 31.6, 28.8, 25.8, 24.8, 22.5, 13.9; HRMS calculated for $C_{11}H_{20}O_3$ ($M^+$), 200.1412, found 200.1422.

Methyl (s)-2-hydroxyoctanoate.

In a 250 mL round bottom flask fitted with a reflux condenser was placed 2.4 g (12 mmol) of (S)-5-hexyl-2,2-dimethyl-1,3-dioxolan-4-one in 150 mL of methanol containing 2 drops of concentrated sulfuric acid. Following heating at reflux for, 6 hours, the reaction mixture was cooled, and 0.5 g of sodium bicarbonate was added. The solvent was evaporated under reduced pressure and the residue dissolved in 200 mL of $CH_2Cl_2$. The solution was washed with 2×75 mL of water, 2×100 mL of saturated sodium bicarbonate solution, and 2×75 mL of brine, and dried ($Na_2SO_4$). The $CH_2Cl_2$ solvent was evaporated under reduced pressure to provide 2.07 g of crude product which was purified over silica gel using ethyl acetate:hexanes (1:5)

to furnish 2.0 g (96%) of the title compound as a pale yellow oil: $[\alpha]_D^{25}$ 2.9° (C=0.8, $CH_3OH$); IR (neat, $cm^{-1}$) 3475 (br), 2925, 2857, 1739; $^1H$ NMR ($CDCl_3$) δ 4.19 (m, 1H), 3.79 (s, 3H), 2.73 (d, J=4.8 Hz, 1H), 1.89–1.75 (m, 1H), 1.72–1.56 (m, 1H), 1.55–1.39 (m, 2H), 1.39–1.28 (m,6H), 0.88 (t, J=6.6 Hz, 3H); HRMS calculated for $C_{19}H_{18}O_3$ ($M^+$), 174.1255, found 174.1255.

Methyl (S)-2-(2-benzyloxy)acetyloxyoctanoate.

In a two-necked, flame-dried 250 mL round bottom flask, under argon, was added 4.28 g (25.0 mmol) of methyl (S)-2-hydroxyoctanoate in 100 mL of anhydrous $CH_2Cl_2$. Benzyloxyacetyl chloride (6.82; 36.9 mmol) was added and the mixture was cooled to 0° C. in an ice-salt bath. Pyridine (2.92 g, 36.9 mmol) was added dropwise. The mixture was stirred for 30 minutes at 0° C., warmed to room temperature, stirred for an additional 3 hours, and quenched with 30 mL of ice-water. An additional 50 mL of $CH_2Cl_2$ was added. Following stirring overnight, the $CH_2Cl_2$ layer was separated, and extracted with 3×50 mL of 10% aqueous HCl solution, 3×75 ml of saturated sodium bicarbonate solution, and 2×100 mL of brine, dried ($Na_2SO_4$) and concentrated under reduced pressure. The residue was purified over silica gel ethyl acetate:hexanes (1:6) as eluant to give 6.7 g (88%) of the title compound as a pale yellow liquid: $[\alpha]_D^{25}$ −10.9°(c=0.3, $CH_3OH$); IR (neat, $cm^{-1}$) 2927, 2859, 1735, 1455; 1438; $^1H$ NMR ($CDCl_3$) δ 7.36–7.29 (m, 5H), 5.11 (t, J=6.5 Hz, 1H), 4.66 (s, 2H), 4.23 (d, J=16.7 Hz, 1H), 4.17 (2, J=16.7 Hz, 1H), 3.75 (s, 3H), 1.87–1.72 (m, 2H), 1.42–1.15 (m, 8H), 0.87 (t, J=6.6 Hz, 3H); HRMS calculated for $C_{18}H_{26}O_5$ ($M^+$), 322. 1780, found 322. 1760.

(S)-3-Benzyloxy-5-hexyl-4-hydroxy-2(5)H-furanone.

In a flame-dried three-necked argon purged 100 mL flask equipped with a low temperature thermometer was added 2.1 g (13.04 mmol) of hexamethyldisilazide in 35 mL of anhydrous tetrahydrofuran. Following cooling to −2° C., 5.3 mL of a 2.5 M n-Buli in hexanes (13.04 mmol) was added dropwise and with stirring while maintaining the temperature below −15° C. The mixture was stirred and held between −3° C. and −5° C. for 45 minutes and cooled to −78° C. Methyl (S)-2-(2-benzyloxyl)acetyloxyoctanoate (2.0 g; 6.21 mmol) in 10 mL of anhydrous tetrahydrofuran was added dropwise. The reaction was stirred for 75 minutes and quenched at −78° C. with 30 mL of precooled 10% aqueous HCl solution. After warming to room temperature the product was extracted with 3×80 mL of ether, and the organic layer was washed with 3×100 mL brine, dried ($Na_2SO_4$) and evaporated under reduced pressure to give 1.65 g of crude white product which was recrystallized using ether/petroleum ether to furnish 1.53 g (85%) of white crystals: mp 74°–75° C.; $[\alpha]_D^{25}$ −18.9° (c=2 0, $CH_3OH$); IR (KBr, $cm^{-1}$) 3035 (br), 2950, 2921, 1735, 1646, 1465; $^1H$ NMR ($CD_3COCD_3$) δ 7.43–7.29 (m, 5H), 5.06 (d, 16.1 Hz, 1H), 5.01 (d, J=16.1 Hz, 1H), 4.69 (dd, J=3.7, 7.0 Hz, 1H), 1.90–1.82 (m, 1H), 1.61–1.45 (m, 1H), 1.38–1.15 (m, 8H), 0.87 (t, J=6.8 Hz, 3H); $^{13}C$ NMR ($CD_3COCD_3$) δ 171.6, 169.4, 161.2, 138.3, 129.2 (2C), 129.1 (2C), 128.9, 120.9, 75.9, 73.4, 32.6, 32.4, 24.4, 23.2, 14.3; HRMS calculated for $C_{17}H_{22}O_4$ ($M^+$), 290.1518; found 290.1538; analysis calculated for $C_{17}H_{22}O_4$ C 70.36, 17.50; found C 70.32, H 7.64.

(S)-5-Hexyl-3,4-dihydroxy-2 (5H)-furanone.

In a two-necked 100 mL round bottom flask was added, under argon, 0.7 g (2.41 retool) of (S)-3-benzyloxy-4-hydroxy-3(5)H-furanone, 0.7 g of 10% Pd/C, and 4.96 g (660.35 mmol) of cyclohexene in 50 mL of absolute ethanol. The mixture was stirred and heated at reflux, filtered (Celite) and the solvent removed under reduced pressure. The residue was recrystallized from acetone/hexanes to provide 0.362 g (75%) of white solid: mp 100°–101° C.; $[\alpha]_D^{25}$ –14.1° (c=0.4, CH$_3$OH); IR (KBr, cm$^{-1}$) 3426 (br), 2921, 1766, 1662; $^1$H NMR (CD$_3$COCD$_3$) δ 4.56 (dd, J=3.4, 7.0 Hz, 1H), 1.98–1.84 (m, 1H), 1.57–1.43 (m, 1H), 1.42–1.22 (m, 8H), 0.90 (t, J=6.7 Hz, 3H); HRMS calculated for C$_{10}$H$_{16}$O$_4$ (M$^+$), 200.1049; found 200.1049; analysis calculated for C$_{10}$H$_{16}$O$_4$: C 60.05, H 8.05.

EXAMPLE 10

(R)-5-(2-Hydroxyethyl)-2,2-dimethyl-1,3 -dioxolan-4-one was prepared in similar yield as for the corresponding S-isomer from the dioxolanate of (S)-malic acid: IR (neat, cm$^{-1}$) 3453 (br), 2994, 2940, 2888, 1791, 1220; $^1$H NMR (CDCl$_3$) δ 4.58 (dd, J=5.1, 7.0 Hz, 1H), 3.91–3.79 (m, 2H), 2.28–2.13 (m, 1H), 2.12–1.97 (m, 1H), 1.64 (s, 3H), 1.57 (s, 3H).

(R)-5-(2 -Hydroxyethyl)-2,2-dimethyl-1,3 -dioxolan-4-one p-toluenesulfonate was prepared in similar yield for the corresponding S-isomer from (R)-5-(2-hydroxyethyl)-2,2-dimethyl-1,3-dioxolane-4-one: mp 52°–53° C.; $[\alpha]_D^{25}$ 3.8° (c=1.1, CH$_3$OH); IR (KBr, cm$^{-1}$) 2992, 1785, 1388, 1357, 1278; $^1$H NMR (CDCl$_3$) δ 7.80 (d, J=8.3 Hz, 2H), 7.36 (d, J=8.3 Hz, 2H), 4.43 (dd, J=4.4, 8.1 Hz, 1H), 4.27–4.14 (m, 2H), 2.46 (s, 3H), 2.30–2.18 (m, 1H), 2.09–1.93 (m, 1H), 1.58 (s, 3H), 1.51 (s, 3H); HRMS calculated for C$_{14}$H$_{18}$O$_6$S (M$^+$), 314. 0824; found 314. 0830.

(R)-5-Hexyl-2,2 -dimethyl-1, 3 -dioxolan-4-one was prepared in similar yield as for the corresponding S-isomer from (R)-5-(2 -hydroxyethyl)-2,2 -dimethyl-1,3 -dioxolan-4-one: $[\alpha]_D^{25}$ –2.9° (c=1.3 CH$_3$OH); IR (neat cm$^{-1}$) 2958 2931, 2859, 1793; $^1$H NMR (CD$_3$Cl$_3$) δ 4.39 (dd, J=4.4, 7.1 Hz, 1H), 1.95–1.81 (m, 1H), 1.81–1.62 (m, 1H), 1.61 (s, 3H), 1.54 (s, 3H), 1.49–1.38 (m, 2H), 1.24–1.28 (m, 6H), 0.89 (t, J=6.6 Hz, 3H); HRMS calculated for C$_{11}$H$_{20}$O$_3$ (M$^+$), 200.1412; found 200.1431.

Methyl (R)-2-hydroxyoctanoate was prepared in similar yield as for the corresponding S-isomer from (R)-5-hexyl-2,2-hexyl-2,2-dimethyl-1,3-dioxolan-4-one: $[\alpha]_D^{25}$ 2.7° (c=0.3, CH$_3$OH); IR (neat, cm$^{-1}$) 3496 (br), 2929, 2859, 1749; $^1$H NMR (CDCl$_3$) δ 4.19 (m, 1H), 3.79 (s, 3H), 2.73 (d, J=4.8 Hz, 1H), 1.89–1.75 (m, 1H), 1.72–1.57 (m, 1H), 1.55–1.39 (m, 2H), 1.39–1.28 (m, 6H), 0.88 (t, J=6.6 Hz, 3H); HRMS calculated for C$_9$H$_{18}$O$_3$ (M$^+$), 174.1255; found 174.1256.

Methyl (R)-2-(2-benzyloxy)acetyloxy was prepared in similar yield as for the corresponding S-isomer from methyl (R)-2-hydroxyoctanoate: $[\alpha]_D^{25}$ 10.8° (c=1.1, CH$_3$OH); IR (KBr, cm$^{-1}$) 2925, 2857, 1733, 1455, 1436; $^1$H NMR (CDCl$_3$) δ 7.36–7.29 (m, 5H), 5.10 (t, J=6.5 Hz, 1H), 4.65 (s, 2H), 4.23 (d, J=16.7 Hz, 1H), 4.17 (d, J=16.7 Hz, 1H), 3.74 (s, 3H), 1.87–1.72 (m, 2H), 1.42–1.15 (m, 8H), 0.87 (t, J=6.6 Hz, 3H); HRMS calculated for C$_{18}$H$_{26}$O$_5$ (M$^+$), 322.1780; found 322.1782.

(R)-3-Benzyloxy-5-hexyl-4-hydroxy-2(5H)-furanone was prepared in similar yield as for the corresponding S-isomer from methyl (R)-2-(2-benzyloxy) acetyloxyoctonoate: mp 86°–87° C.; $[\alpha]_D^{25}$ 18.8° (c=0.9, CH$_3$OH); IR (KBr, cm$^{-1}$) 3035 (br), 2950, 2921, 1735; 1646; 1465; $^1$H NMR (CD$_3$COCD$_3$) δ 7.43–7.29 (m, 5H), 5.07 (d, 16.2, 1H), 5.01 (d, J=16.2, 1H), 4.69 (dd, J=3.7, 7.0, 1H), 1.90–1.82 (m, 1H), 1.61–1.45 (m, 1H), 1.61–1.45 (m, 1H), 1.38–1.15 (m, 8H), 0.87 (t, J=6.7 Hz, 3H); HRMS calculated for C$_{17}$H$_{22}$O$_4$ (M$^+$), 290.1518, found 290.1505.

(R)-5-Hexyl-3,4-dihydroxy-2(5H)-furanone was prepared in similar yield as for the corresponding S-isomer from (R)-3 -benzyloxy-5-hexyl-4-hydroxy-2 (5H)-furanone:

mp 98°–99° C.; $[\alpha]_D^{25}$ 14.2° (c=1.9, CH$_3$OH); IR (KBr, cm$^{-1}$) 3423 (br), 2921, 1768, 1660; $^1$H NMR (CD$_3$COCD$_3$) δ 4.57 (dd, J=3.4, 7.0 Hz, 1H), 1.98–1.84 (m, 1H), 1.57–1.43 (m, 1H), 1.42–1.22 (m, 8H), 0.90 (t, J=6.7 Hz, 3H); HRMS calculated for C$_{10}$H$_{16}$O$_4$ (M$^+$), 200.1049; found 200.1049.

What is claimed is:

1. An optically pure compound of the general formulae Ia or Ib:

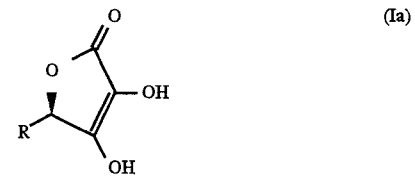

(Ia)

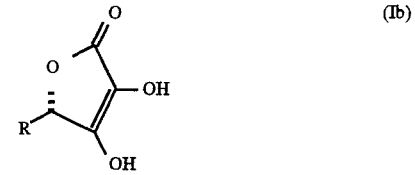

(Ib)

wherein R is an alkenyl group of 2–20 carbon atoms containing one or more degrees of unsaturation, or a physiologically acceptable salt thereof.

2. A compound according to claim 1 which is (S)-3,4-dihydroxy-5-[(Z)-3-octadecenyl]-2(5H)-furanone.

3. A compound according to claim 1 which is (R)-3,4-dihydroxy-5-[(Z)-3-octadecenyl]-2(5H)-furanone.

4. A compound according to claim 1 which is (S)-3,4-dihydroxy-5-[(all-Z)-3,6,9,12-octadecatetraenyl-2(5H)-furanone.

5. A compound according to claim 1 which is (R)-3,4-dihydroxy-5-[(all-Z)-3,6,9,12-octadecatetraenyl]-2(5H)-furanone.

6. A pharmaceutical composition comprising an effective amount of a compound selected from the group consisting of an optically pure compound of formulae Ia or Ib:

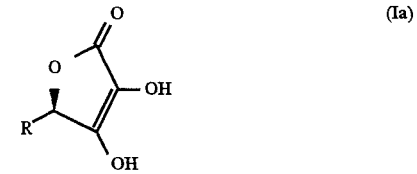

(Ia)

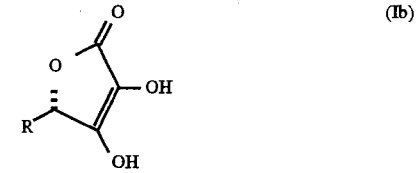

(Ib)

wherein R is an alkenyl group of 2–20 carbon atoms containing one or more degrees of unsaturation, or a physiologically acceptable salt thereof, in combination with a pharmaceutically acceptable carrier therefor.

7. A composition according to claim 6 which is (S)-3,4-dihydroxy-5-[(Z)-3 -octadecenyl]-2(5H)-furanone.

8. A composition according to claim 6 which is (R)-3,4-dihydroxy-5-[(Z)-3-octadecenyl]-2(5H)-furanone.

9. A composition according to claim 6 which is (S)-3,4 -dihydroxy-5-[(all-Z)-3,6,9,12-octadecatetraenyl]-2(5H)-furanone.

10. A composition according to claim 6 which is (R)-3, 4-dihydroxy-5-[(all-Z)-3,6,9,12-octadecatetraenyl]-2(5H)-furanone.

11. A process for the preparation of compounds of the formula I

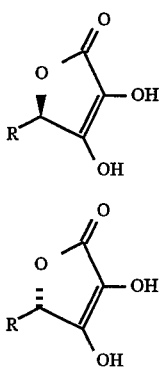

wherein R' is an alkenyl or alkanyl group of 2–20 carbon atoms, and when an alkenyl group, contains one or more degrees of unsaturation, or an aryl group; which comprises (a) coupling of allyloxyacetic acid with the optically pure alkanyl ester of the formula II

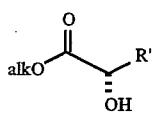

or its corresponding isomer, wherein R' is as hereinbefore defined and alk is a lower alkanyl group of 1–6 carbon atoms in the presence of DCC and an acid acceptor to obtain an allyloxy ester of the formula III

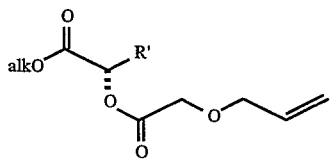

or its corresponding isomer, wherein alk and R' are as hereinbefore defined;

(b) cyclizing the allyl ester of formula III with LiHMDA to afford the allyloxy tetronic acid of the formula IV

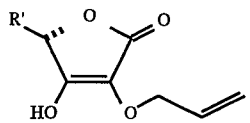

or its corresponding isomer, wherein R' is as hereinbefore defined;

(c) isomerizing the allyloxy aci-reductone of formula IV with hydrogen and an iridium catalyst to yield the corresponding 1-propenyl ether of the formula V

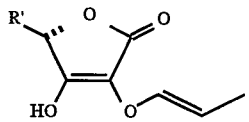

or its corresponding isomer, wherein R' is as hereinbefore defined; and (d) hydrolysis of the enol ether of formula V or its corresponding isomer with aqueous acid, to afford the desired compound of formula I.

12. The process according to claim 11 wherein the coupling of step (a) is effected using methylene chloride as a solvent.

13. The process according claim 11 wherein the cyclization of step (b) is effected using approximately 2 equivalents of LiHMDA at approximately −78° C.

14. The process according to claim 11 wherein the isomerization of step (c) is effected using [Bis(methyldiphenylphosphine](1,5-cyclooctadiene)iridium (1) hexafluorophosphate as the catalyst.

15. The process according to claim 11 wherein the acid hydrolysis of step (d) is effected with 50% aqueous acetic acid.

16. A method of treating or preventing atherosclerotic disorders which comprises administering to a mammal in need of such therapy an effective amount of a compound selected from the group consisting of an optically pure compound of formulae Ia or Ib:

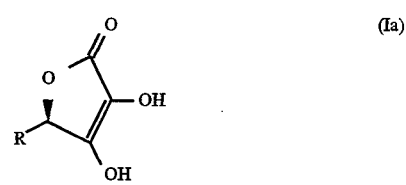

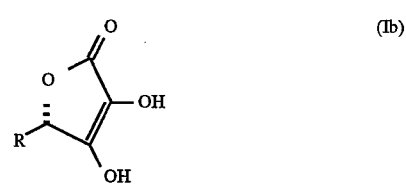

wherein R is an alkenyl group of 2–20 carbon atoms containing one or more degrees of unsaturation, or a physiologically acceptable salt thereof, in combination with a pharmaceutically acceptable carrier therefor.

17. A method according to claim 16 which is (S)-3,4-dihydroxy-5-[(Z)-3-octadecenyl]-2(5H)-furanone.

18. A method according to claim 16 which is (R)-3,4-dihydroxy-5-[(Z)-3-octadecenyl]-2(5H)-furanone.

19. A method according to claim 16 which is (S)-3,4-dihydroxy-5-[(all-Z)-3,6,9,12-octadecatetraenyl]-2(5H)-furanone.

20. A method according to claim 16 which is (R)-3,4-dihydroxy-5-[(all-Z)-3,6,9,12-octadecatetraenyl]-2(5H)-furanone.

21. A method of inhibiting inflammatory cytokines which comprises administering to a mammal in need of such therapy an effective amount of a compound selected from the group consisting of an optically pure compound of formulae Ia or Ib:

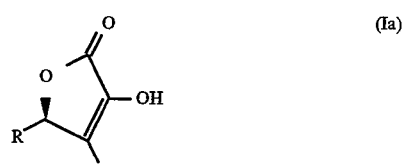

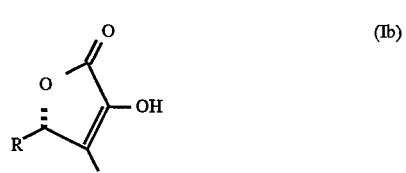

wherein R is an alkenyl group of 2–20 carbon atoms or an alkanyl group of 9–20 carbon atoms, and when an alkenyl group, contains one or more degrees of unsaturation, or a physiologically acceptable salt thereof, in combination with a pharmaceutically acceptable carrier therefor.

22. A method according to claim 21 wherein R is an alkanyl group of 9–20 carbon atoms.

23. A method according to claim 21 which is (S)-3,4-dihydroxy-5-[3-octadecanyl]-2(5)H-furanone.

24. A method according to claim 21 which is (R)-3,4-dihydroxy-5-[3-octadecanyl]-2(5H)-furanone.

25. A method according to claim 21 wherein R is an alkenyl group of 2–20 carbon atoms.

26. A method according to claim 21 which is (S)-3,4-dihydroxy-5-[(Z)-3-octadecenyl]-2(5)H-furanone.

27. A method according to claim 21 which is (R)-3,4-dihydroxy-5-[(Z)-3-octadecenyl]-2(5)H-furanone.

28. A method according to claim 21 which is (S)-3,4-dihydroxy-5-[(all-Z)-3,6,9,12-octadecatetraenyl]-2(5H)-furanone.

29. A method according to claim 21 which is (R)-3,4-dihydroxy-5-[(all-Z)-3,6,9,12-octadecatetraenyl]-2(5)H-furanone.

30. A method according to claim 21 wherein the inflammatory cytokine is present in rheumatoid arthritis.

31. A method according to claim 21 wherein the inflammatory cytokine is present in acute or chronic inflammation.

32. A method according to claim 21 wherein the inflammatory cytokine is present in multiple sclerosis.

33. A method according to claim 21 wherein the inflammatory cytokine is present in septic shock syndrome.

34. A method according to claim 21 wherein the inflammatory cytokine is present in cachexia.

* * * * *